United States Patent
Burkhart et al.

(10) Patent No.: US 11,642,120 B2
(45) Date of Patent: *May 9, 2023

(54) TENSIONABLE KNOTLESS ANCHORS AND METHODS OF TISSUE REPAIR

(71) Applicant: Arthrex, Inc., Naples, FL (US)

(72) Inventors: Stephen S. Burkhart, Boerne, TX (US); Derek C. Sullivan, Naples, FL (US); William C. Benavitz, Naples, FL (US); Thomas Dooney, Jr., Naples, FL (US); Lee D. Kaplan, Miami, FL (US); James P. Bradley, Pittsburgh, PA (US)

(73) Assignee: Arthrex, Inc., Naples, FL (US)

( * ) Notice: Subject to any disclaimer, the term of this patent is extended or adjusted under 35 U.S.C. 154(b) by 515 days.

This patent is subject to a terminal disclaimer.

(21) Appl. No.: 16/775,708

(22) Filed: Jan. 29, 2020

(65) Prior Publication Data
US 2020/0170634 A1 Jun. 4, 2020

Related U.S. Application Data

(63) Continuation-in-part of application No. 15/352,246, filed on Nov. 15, 2016, now Pat. No. 10,631,845, which is a continuation-in-part of application No. 15/004,154, filed on Jan. 22, 2016, now Pat. No. 10,172,606.

(51) Int. Cl.
 *A61B 17/04* (2006.01)
 *A61F 2/08* (2006.01)
 *A61B 17/56* (2006.01)

(52) U.S. Cl.
 CPC ........ *A61B 17/0401* (2013.01); *A61F 2/0811* (2013.01); *A61B 2017/044* (2013.01); *A61B 2017/0414* (2013.01); *A61B 2017/0427* (2013.01); *A61B 2017/0496* (2013.01); *A61B 2017/564* (2013.01); *A61F 2002/0852* (2013.01); *A61F 2002/0888* (2013.01)

(58) Field of Classification Search
 CPC ........ A61B 17/0401; A61B 2017/0414; A61B 2017/0427; A61B 2017/044; A61B 2017/0496; A61B 2017/564; A61B 2017/0409; A61B 2017/0412; A61B 2017/0477; A61B 2017/0445; A61B 2017/0458; A61B 90/92; A61F 2/0811; A61F 2002/0852; A61F 2002/0888
 See application file for complete search history.

(56) References Cited

U.S. PATENT DOCUMENTS

| | | | |
|---|---|---|---|
| 6,716,234 B2 | 4/2004 | Grafton et al. | |
| 7,329,272 B2 | 2/2008 | Burkhart et al. | |
| 7,713,285 B1 * | 5/2010 | Stone | A61F 2/0811 606/232 |
| 7,892,256 B2 | 2/2011 | Grafton et al. | |
| 8,012,174 B2 | 9/2011 | ElAttrache et al. | |
| 9,005,246 B2 | 4/2015 | Burkhart et al. | |

(Continued)

*Primary Examiner* — Richard G Louis
*Assistant Examiner* — Chima U Igboko
(74) *Attorney, Agent, or Firm* — Blank Rome LLP

(57) ABSTRACT

Surgical devices and methods of tissue repair using tensionable knotless fixation devices. A flexible material (for example, suture or suture tape) may be attached to the fixation device. A flexible material may be threaded through an eyelet of a tip provided as part of a swivel anchor assembly to provide added stability to the fixation devices.

18 Claims, 29 Drawing Sheets

(56) References Cited

U.S. PATENT DOCUMENTS

| | | |
|---|---|---|
| 9,107,653 B2 | 8/2015 | Sullivan |
| 2008/0004659 A1 | 1/2008 | Burkhart |
| 2009/0248068 A1 | 10/2009 | Lombardo |
| 2009/0312794 A1 | 12/2009 | Nason |
| 2010/0160962 A1 | 6/2010 | Dreyfuss |
| 2010/0179573 A1 | 7/2010 | Levinsohn |
| 2011/0118762 A1 | 5/2011 | Dooney, Jr. |
| 2012/0041484 A1 | 2/2012 | Briganti |
| 2012/0150226 A1 | 6/2012 | Burkhart |
| 2013/0023928 A1 | 1/2013 | Dreyfuss |
| 2013/0023929 A1 | 1/2013 | Sullivan |
| 2013/0096611 A1* | 4/2013 | Sullivan ............. A61B 17/0485 606/232 |
| 2013/0165972 A1 | 6/2013 | Sullivan |
| 2013/0296936 A1 | 11/2013 | Burkhart |
| 2013/0345750 A1 | 12/2013 | Sullivan |
| 2015/0297211 A1 | 10/2015 | Sullivan |
| 2017/0209135 A1 | 7/2017 | Sullivan |
| 2017/0209139 A1 | 7/2017 | Burkhart |

* cited by examiner

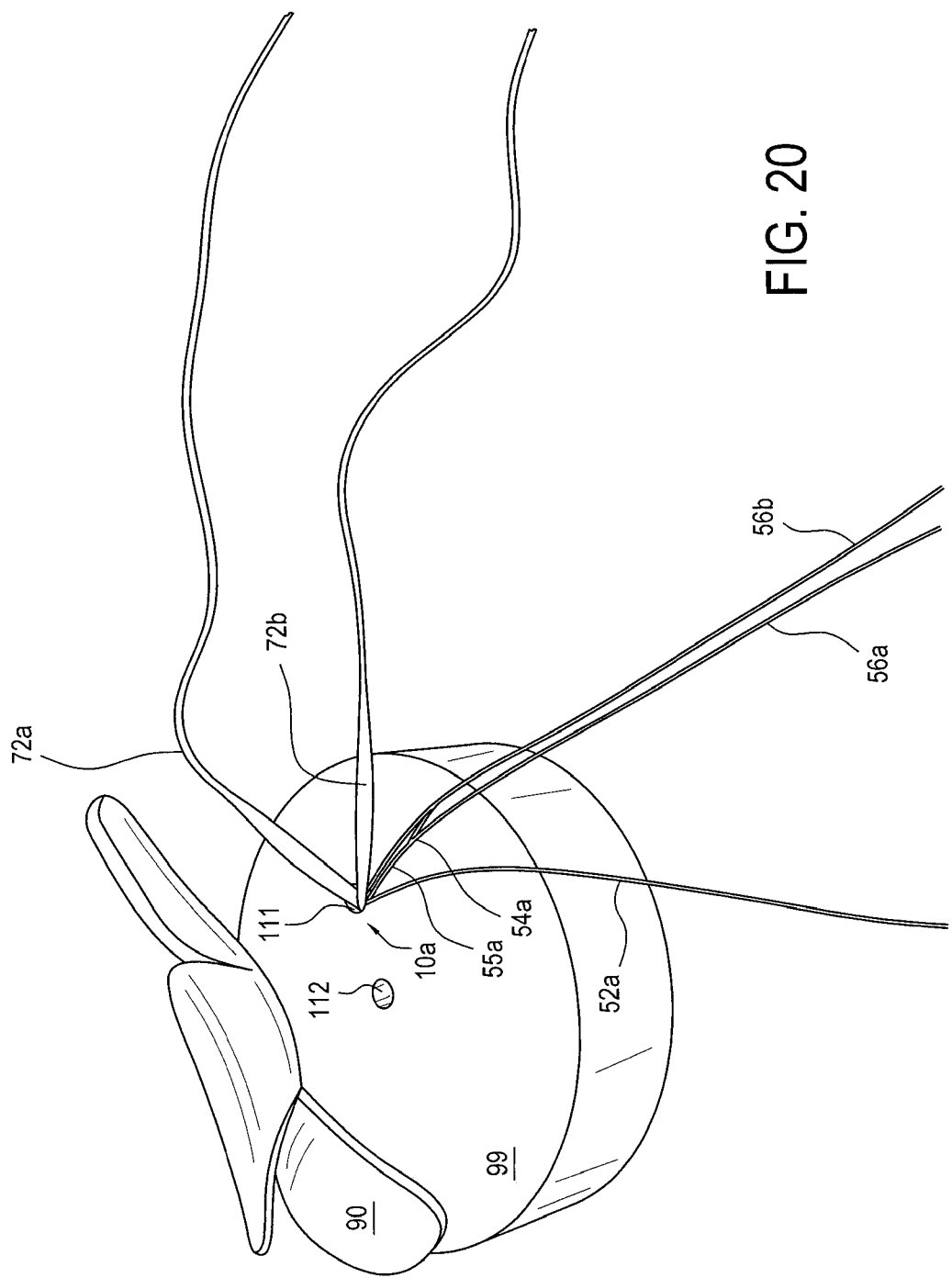

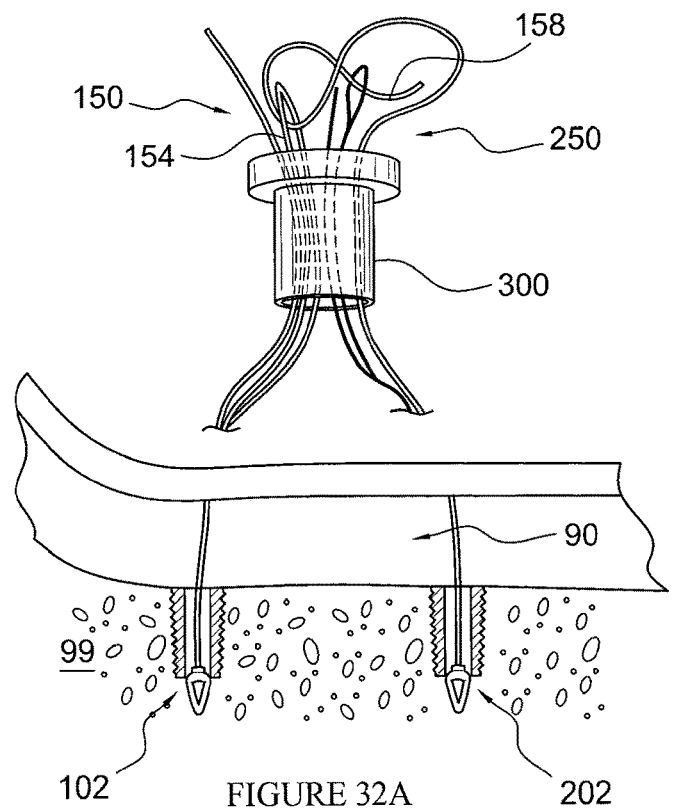
FIGURE 32A
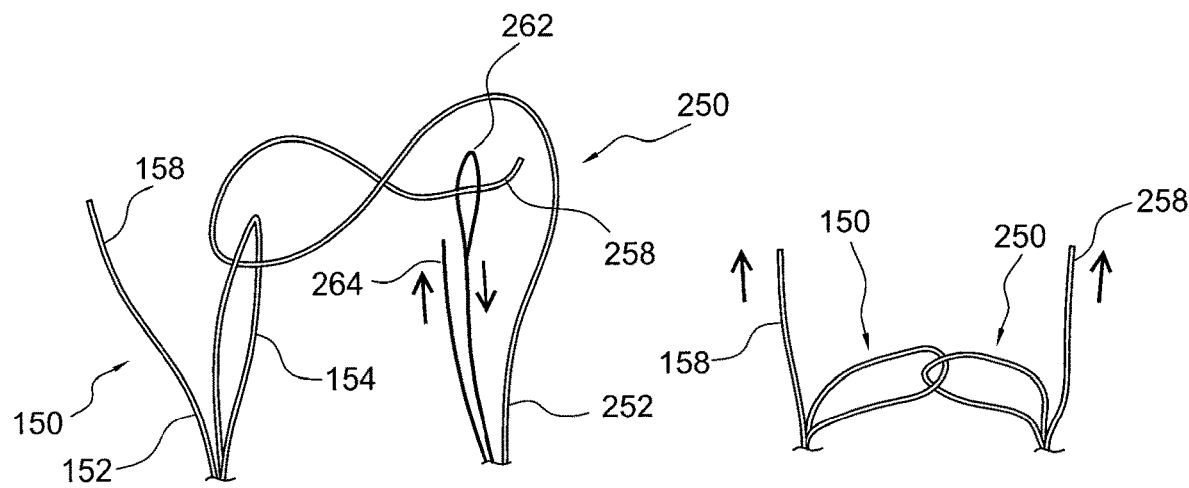
FIGURE 32B
FIGURE 32C

TENSIONABLE KNOTLESS ANCHORS AND METHODS OF TISSUE REPAIR

RELATED APPLICATION

This application is a continuation-in-part of U.S. application Ser. No. 15/352,246, filed on Nov. 15, 2016, which is a continuation-in-part of U.S. application Ser. No. 15/004,154, filed on Jan. 22, 2016, now U.S. Pat. No. 10,172,606, the subject matter of which is herein incorporated by reference in its entirety.

BACKGROUND

The present disclosure relates to surgical devices and methods and, more particularly, to surgical devices and methods for use in tissue repair.

SUMMARY

Surgical assemblies, systems and techniques for knotless soft tissue repair and fixation, such as fixation of soft tissue (ligament, tendon, graft, etc.) to bone, are disclosed. Surgical assemblies comprise tensionable knotless fixation devices that are inserted into bone. A tensionable knotless fixation device is provided with a tensioning construct (formed of a tensioning strand, a tensionable, adjustable, knotless, self-cinching loop, and a splice adjacent the loop) pre-loaded onto a fixation device. A flexible material (for example, suture or suture tape) may be attached to a fixation device. A flexible material may be threaded through an eyelet of a fixation device.

Methods of soft tissue repair which do not require tying of knots and allow adjustment of both tension of suture and location of tissue with respect to bone are also disclosed.

An exemplary method includes the steps of providing a first fixation device preloaded with a tensionable construct; providing a second fixation device with a non-pre-looped tensionable construct; anchoring the first and second fixation devices in bone such that the first and second fixation devices are arranged in a medial row; passing the pre-loaded tensionable construct of the first fixation device and the non-pre-looped tensionable construct of the second fixation device through tissue; threading a free end of a flexible strand of the non-pre-looped tensionable construct through a tensionable loop of the pre-looped tensionable construct and then subsequently passing the free end of the non-pre-looped tensionable construct through an eyelet of a passing device coupled with the flexible strand of the non-pre-looped tensionable construct; and pulling on a tail end of the passing device to thread the free end of the flexible strand of the first fixation device through a splice in itself, thereby forming two interlocking loops outside of the tissue. This exemplary method may also include the steps of preloading the first and second fixation devices with first and second flexible materials, respectively; passing first and second limbs of the first and second flexible materials through the tissue proximal to the pre-looped tensionable and non-pre-looped tensionable constructs; tightening or tensioning the two interlocking loops by pulling on a free end of the pre-looped tensionable construct and the free end of the non-pre-looped tensionable construct; and securing the first and second ends of the first and second flexible material to bone with additional fixation devices.

An exemplary embodiment includes a device for tissue repairs comprises an anchor body that comprises a central shaft and an outer surface having a fixation structure for securing the anchor body in a bone hole; a tip that has a first end, a second end, a longitudinal axis extending between the first and second ends, and a recess that extends transverse to the longitudinal axis for receiving a flexible member, wherein the first end of the tip is separable from and connectable to the anchor body; and a tensionable construct that is fixedly connected to the tip and comprising a flexible strand defining two apertures at different locations along a length of the flexible strand, and a channel extending through the flexible strand and connecting the two apertures, for forming a splice and a loop with an adjustable perimeter adjacent the splice. A portion, such as a post, of the tip is positionable between two portions of the flexible strand in a direction perpendicular to the longitudinal axis, and the two portions of the flexible strand are configured to extend away from the second end of the tip.

In some embodiments the two portions of the flexible strand are configured to be connected to one another in a region between the portion of the tip and the second end of the tip; the portion of the tip comprises a post, and wherein the flexible strand is configured to extend around a side of the post closest to the second end; the two portions of the flexible strand are further configured to be connected to one another on a side of the post closest to the first end; the channel through the flexible strand forms a coreless portion of the flexible strand; the flexible strand is configured to extend through the anchor body; the flexible strand further comprises the splice formed at the channel and the loop, wherein the loop is a knotless, tensionable, self-cinching loop with the adjustable perimeter; when the knotless, tensionable, self-cinching loop is formed, two separate segments of the flexible strand extend around the tip between the portion of the tip and the second end of the tip; the flexible strand further comprises a free end at a side opposite the fixed connection; the splice and loop are formed by threading the free end of the flexible strand through the channel of the flexible strand, wherein the loop formed is a knotless, tensionable, self-cinching loop with the adjustable perimeter, and wherein the free end of the flexible strand forms a tensioning suture limb for reducing the perimeter of the knotless, tensionable, self-cinching loop; the flexible member held in the opening or recess; and/or the flexible member is releasably attached to the tip.

In other embodiments, the fixation structure on the outer surface of the anchor body comprises a thread, ribs, ridges, and/or barbs; the tip and the anchor body are rotatable relative to one another when the first end of the tip is connected to the anchor body, such that the tip and the anchor body together form a swivel anchor; the opening or recess forms an eyelet that extends through the tip; the first end of the tip is insertable into the anchor body; and/or a passer device is pre-loaded through the channel of the flexible strand, wherein both ends of the passer device are configured to extend through the anchor body.

Another exemplary embodiment includes a method of stabilizing a bone or joint lesion with at least two fixation devices for tissue repair, where each fixation device comprises an anchor body that comprises a central shaft and an outer surface having a fixation structure for securing the anchor body in a bone hole, a tip having a first end, a second end, a longitudinal axis extending between the first and second ends, and an opening or recess extending transverse to the longitudinal axis for receiving a flexible member, wherein the first end of the tip is separable from and connectable to the anchor body, and a tensionable construct fixedly connected to the tip and comprising a flexible strand defining two apertures at different locations along a length of the flexible strand, and a channel that extends through the flexible strand and connecting the two apertures, for forming a splice and a loop with an adjustable perimeter adjacent the splice; and a portion, such as a post, of the tip is positionable between two portions of the flexible strand in a direction perpendicular to the longitudinal axis, and wherein the two portions of the flexible strand are configured to extend away from the second end of the tip. The method comprises implanting a first fixation device into a first bone hole by inserting the tip and thereafter separately securing the anchor body to the tip in the first bone hole, with the tensionable construct extending into and through the anchor body; implanting a second fixation device into a second bone hole by inserting the tip and thereafter separately securing the anchor body to the tip in the second bone hole, with the tensionable construct extending into and through the anchor body; passing free ends of the flexible strands of the two fixation devices through different locations of tissue; passing the free end of the flexible strand of the first fixation device through the channel of the flexible strand of the second fixation device, and passing the free end of the flexible strand of the second fixation device through the channel of the flexible strand of the first fixation device; and pulling each of the free ends of the flexible strands after passing the respective free ends through the respective channels, such that the flexible strands of both the first and second fixation devices compress the tissue between the first and second bone holes relative to the bone.

In an embodiment of the method, each of the fixation devices further comprises the flexible member held in the opening or recess, wherein the flexible member is separate from the tensionable construct and is configured to form at least one further connection separate from connections formed by the flexible strands of the first and second fixation devices.

In an embodiment, the method further comprises securing respective first sections of the flexible member of the first and second fixation devices to a third fixation device and securing the third fixation device into a third bone hole, and securing respective second sections of the flexible member of the first and second fixation devices to a fourth fixation device and securing the fourth fixation device into a fourth bone hole.

Other objects, advantages and salient features of the invention will become apparent from the following detailed description, which, taken in conjunction with the annexed drawings, discloses preferred embodiments of the present invention.

BRIEF DESCRIPTION OF THE DRAWINGS

FIGS. 20-30 illustrate an exemplary method of tissue repair with the fixation device of FIG. 1.

FIGS. 32A-32D illustrate exemplary method of tissue repair using the fixation devices of FIGS. 31A-B.

FIGS. 37A and 37B, and FIGS. 37C and 37D, illustrate an anchor construct as a pre-looped tensionable loop construct, depicted after the anchor has been inserted into the bone, and an anchor construct that is a non-pre-looped tensionable loop construct, depicted after the anchor has been inserted into the bone, respectively.

DETAILED DESCRIPTION

Figure 1:
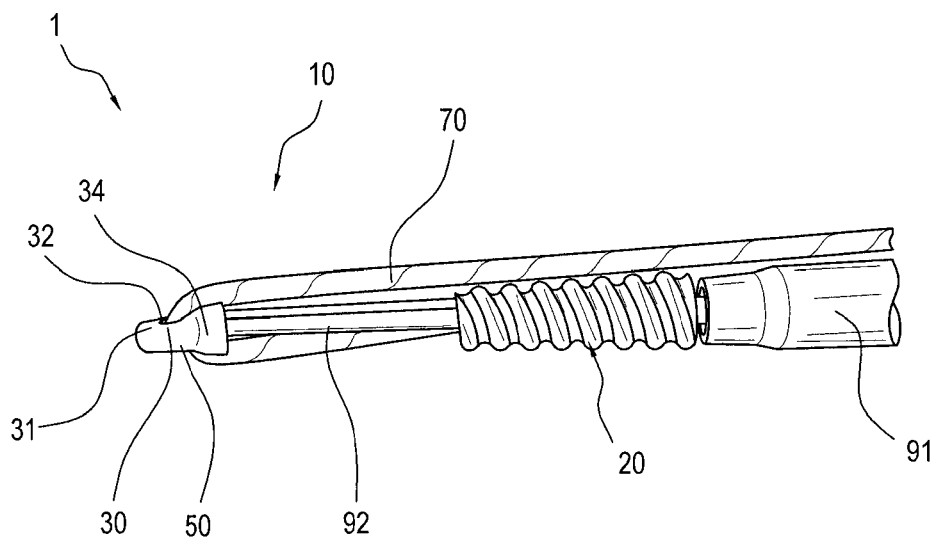
FIGS. 1 and 2 illustrate an exemplary embodiment of a fixation device loaded onto a driver.

Surgical assemblies, systems and techniques for knotless soft tissue repair and fixation, such as fixation of soft tissue (ligament, tendon, graft, etc.) to bone, are disclosed. Surgical assemblies comprise tensionable knotless fixation devices that are inserted into bone. Tensionable knotless fixation devices are provided with a tensioning construct (formed of a tensioning strand, a tensionable, adjustable, knotless self-cinching loop, and a splice adjacent the loop) pre-loaded onto the fixation device. A flexible material (for example, suture or suture tape) may be attached to the fixation device, for example, by being threaded through an eyelet of the fixation device.

As detailed below, the surgical assemblies and devices disclosed allow for knotless fixation of tissue using an eyelet suture of a fixation device (for example, a suture anchor with an eyelet or a SwiveLock® anchor). A mechanism inside the suture eyelet is similar to the knotless tensionable construct of the SutureTak®, except that there is no post or similar device within the anchor body to allow suture to wrap around. The knotless tensionable construct passes the anchor body of modified SwiveLock® anchors. In this manner, the surgical assemblies and devices detailed below combine two technologies to provide a strong knotless repair, as well as a backup knotless repair separate from a first repair.

Methods of soft tissue repair which do not require tying of knots and allow adjustment of both the tension of the suture and the location of the tissue with respect to the bone are also disclosed.

A surgical assembly can include (i) a fixation device; (ii) a tensionable construct pre-loaded on the fixation device; and (iii) a flexible material (for example, suture or suture tape) attached to the fixation device. A flexible material may be also pre-loaded on the fixation device, and may be releasably attached to the fixation device, or securely fixed to it. The fixation device can include an anchor body insertable over an anchor tip, the anchor tip including a shaft attached to an anchor tip body, the anchor tip body being provided with first and second apertures or openings (for example, an eyelet oriented in a first direction and a through-hole or passage oriented in a second direction, which may be different from the first direction). A tensionable construct may be pre-loaded on the fixation device. The tensionable construct may consist of a flexible strand with a knot and a free end, a splice and an adjustable, tensionable, self-cinching, knotless, closed loop having an adjustable perimeter, located adjacent the splice. The tensionable construct passes through the anchor tip and extends through at least a portion of the anchor body of the fixation device.

The fixation device may be a SwiveLock® anchor as disclosed and described, for example, in U.S. Pat. No. 8,012,174 issued Sep. 6, 2011, U.S. Pat. No. 9,005,246 issued Apr. 14, 2015, and US 2013/0296936 published Nov. 7, 2013, the disclosures of all of which are fully incorporated by reference in their entirety herein, with or without a modified eyelet in the anchor tip, and as detailed below.

The flexible material (suture construct) can be any suture strand or suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. However, the fixation devices detailed below can be used with any type of flexible material or suture known in the art.

The tensionable construct may use a mechanism similar to that of knotless SutureTak® but provides variations and improvements in the design of the tensioning construct. Details of the formation of an exemplary tensioning construct employed in the embodiments of the present invention detailed below are set forth in U.S. Pat. No. 9,107,653 issued Aug. 18, 2015; US 2013/0165972, entitled "Tensionable Knotless Anchor Systems and Methods of Tissue Repair;" and US 2013/0345750, entitled "Tensionable Knotless Labral Anchor and Methods of Tissue Repair," the disclosures of all of which are incorporated by reference in their entirety herein.

The tensionable construct may be formed of a flexible strand or flexible material that is easily spliced through itself to form a splice and a knotless, self-cinching, adjustable, closed loop with an adjustable perimeter. The flexible strand or material may be made of any known suture material, such as ultrahigh molecular weight poly ethylene (UHMWPE) or FiberWire® suture (disclosed in U.S. Pat. No. 6,716,234 the disclosure of which is herein incorporated by reference in its entirety), and can be braided or multi-filament. For example, the suture can be UHWMPE suture without a core to permit ease of splicing.

FIG. 1 illustrates an exemplary embodiment of a fixation device 10 (tensionable knotless fixation device 10) seated on a driver 91. Tensionable knotless fixation device 10 comprises an anchor body 20 and an anchor tip 30, the anchor body 20 being insertable over the anchor tip 30. A tensionable construct 50 (also referred to as "tensioning construct 50") and a flexible material 70 are pre-loaded on the fixation device 10 to form surgical assembly 1. Tensionable knotless fixation device 10 is seated on driver 91. Driver 91 has a thin cannulated rod 92, where anchor tip 30 is seated at the proximal end 94 of the thin cannulated rod 92. Anchor body 20 is cannulated and is fully seated around thin cannulated rod 92.

Tensionable construct 50 is pre-loaded onto the fixation device 10, and extends through at least a portion of the fixation device. Flexible material 70 may be also pre-loaded onto the fixation device 10.

Anchor tip 30 includes anchor tip body 31 attached to a cannulated shaft 36 (not shown in FIG. 1), wherein the cannulated shaft 36 is at least partially disposed within thin cannulated rod 92 of driver 91. Anchor tip body 31 is also provided with first and second through-holes, openings, or passages 32, 34. In an exemplary embodiment, one of the first and second through-holes, openings, or passages is an eyelet 32 having a first orientation relative to a longitudinal axis of the anchor tip, and the other of the first and second-through holes, openings, or passages is a flexible material hole or passage 34 (a transverse opening 34) having a second orientation relative to a longitudinal axis of the anchor tip. In an exemplary embodiment, the first orientation is different from the second orientation. In another exemplary embodiment, the first orientation is about perpendicular to the second orientation. Eyelet 32 accommodates and houses tensionable construct 50. Hole, opening, or passage 34 accommodates and houses flexible material 70.

Figure 2:
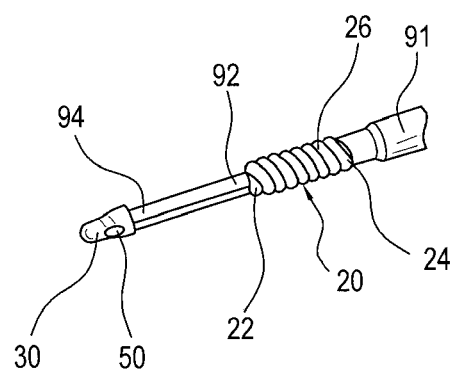

FIG. 2 illustrates another view of tensionable knotless fixation device 10 pre-loaded with tensionable construct 50 but without flexible material 70.

During installation of fixation device 10, anchor body 20 is assembled onto the operational end of the driver 91. Anchor tip 30 is threaded or otherwise attached onto the tip of thin cannulated rod 92. Anchor tip 30 is then placed within a prepared bone hole or tunnel until anchor tip 30 reaches the bottom of the bone hole or tunnel, or reaches the desired depth. At this point, anchor body 20 is still outside of the bone hole or tunnel. Anchor body 20 is then reduced down thin cannulated rod 92 (advanced down the cannulated rod to be insertable over the anchor tip 30) by holding a thumb pad (not pictured) as the inserter handle (not pictured) of the driver 91 is turned clockwise. When anchor body 20 is fully seated, cannulated shaft 36 of anchor tip 30 is fully engaged by cannulated anchor body 20, creating a stable swivel construct of the fixation device 10 wherein anchor tip 30 is rotatably secured to anchor body 20.

In an exemplary embodiment, anchor body 20 is cannulated and has a proximal end 22 and a distal end 24, wherein proximal end 22 is the end closest to anchor tip 30. The exterior 26 of anchor body 20 can be threaded, for example like a screw, or can be any suitable means for securing in a bone hole or tunnel, for example, in the form of circumferential ridges extending radially. The exterior 26 of anchor body 20 is responsible for both securing fixation device 10 in the bone hole or tunnel, as well as securing, by friction or interference fit, suture construct 70 against the bone wall and exterior 26 of anchor body 20.

Anchor body 20 (in the form of a cannulated fixation device 20 or cannulated screw 20) may be pre-loaded onto the shaft of the driver. The anchor tip 30 (implant 30) is designed to be releasably attached (by a snap fit, for example) to a distal end of the driver and to swivel relative to the anchor body 20 (cannulated fixation device 20). The anchor tip (implant) with attached suture is anchored into bone by rotating the driver to rotate and advance the anchor body 20 (cannulated fixation device 20) while keeping the anchor tip 30 (implant 30) stationary, thereby securing the suture and providing tissue fixation without tying knots in the suture. The driver with the cannulated rod (passing slidably and rotatably through a cannulated driver assembly of the driver) has a tip adapted to accept the anchor tip 30 (implant 30), to allow the anchor tip 30 to be loaded onto the rod and be fully seated on an end of the shaft of the driver.

The anchor tip 30 (implant 30) is rotatably received within the anchor body 20 upon advancement of the anchor body 20 over a shaft of the anchor tip 30, the anchor tip 30 being configured to receive the tensionable construct and the flexible material. The anchor tip has a closed aperture or eyelet to receive the flexible material (suture or suture tape) to be attached to bone. The anchor tip 30 may be a metal tip or non-metal tip (e.g., plastic or polymer), and the anchor body 20 may have a cylindrical, screw-like configuration (for example, a cannulated interference screw).

Flexible material 70 can comprise any type of flexible material or suture known in the art, preferably suture tape such as Arthrex FiberTape®, or combination of suture and suture tape, among many others. Flexible material 70 can be configured to be pre-loaded or threaded through eyelet 32 of anchor tip 30. A first limb 72a and a second limb 72b pass outside of anchor body 20 and are secured against the bone wall and exterior 26 by friction or interference fit. In an exemplary embodiment, first limb 72a and second limb 72b can terminate into a single suture passing limb 74 to simplify passing each of limbs 72a and 72b through tissue. In this manner, both limbs 72a and 72b can be passed at the same time. After passing limb 74 is passed through tissue, it can be cut and removed, leaving first limb 72a and second limb 72b separated and passed through tissue.

In another embodiment, first limb 72a and second limb 72b do not terminate into a single passing limb, and are passed through tissue separately. In this embodiment, flexible material 70 may or may not be pre-loaded through eyelet 32 of anchor tip 30. In another embodiment, first limb 72a and second limb 72b do not terminate into a single suture passing limb, but both are loaded into a suture passer together and passed together.

Figure 3:
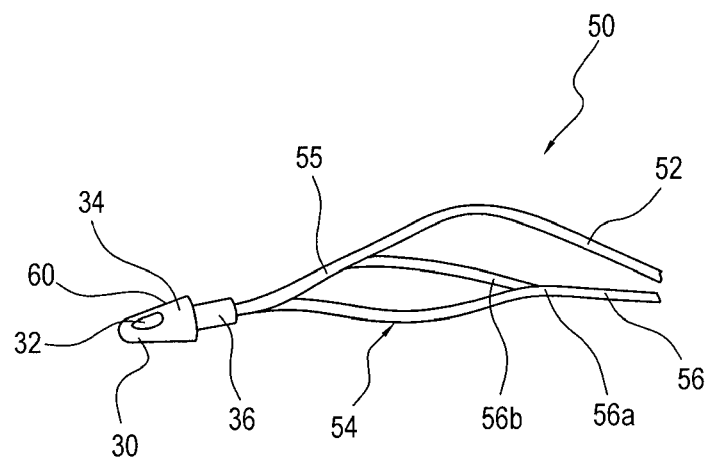
FIGS. 3 and 4 illustrate an exemplary embodiment of an anchor tip loaded with a tensioning construct.

FIG. 3 illustrates an exemplary embodiment of anchor tip 30 with tensionable construct 50 preloaded onto anchor tip 30. Tensionable construct 50 comprises a tensioning strand 52, a tensionable loop 54, a splice 55, and fixed loop strands 56a and 56b of stand 56 attached to loop 54. Fixed loop strands 56a and 56b pass through tensionable loop 54 and can terminate into a single loop strand 56. Loop strand 56 and tensioning strand 52 can then terminate into a single tensioning construct passing limb 58. In another embodiment, loop strands 56a and 56b do not terminate into a single loop strand 56, but instead terminate along with tensioning strand 52 into tensioning construct passing limb 58. In this embodiment, three limbs terminate into one limb at the same place. Tensioning construct passing limb 58 can be passed through tissue and then cut and removed. Loop strands 56a and 56b can then be discarded, leaving tensioning strand 52 and tensionable loop 54 passed through the tissue. Multiple tensionable loop strands may be provided attached to loop 54 (for example, passed through the loop 54). Loop 54 is a knotless, tensionable, adjustable, self-cinching loop having an adjustable perimeter.

Figure 4:
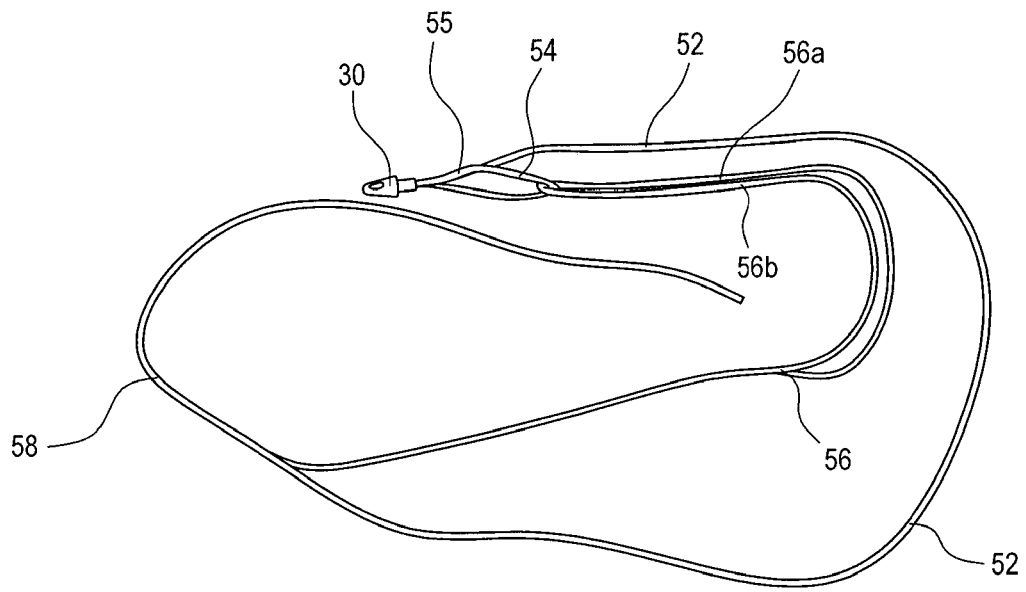
Figure 5:
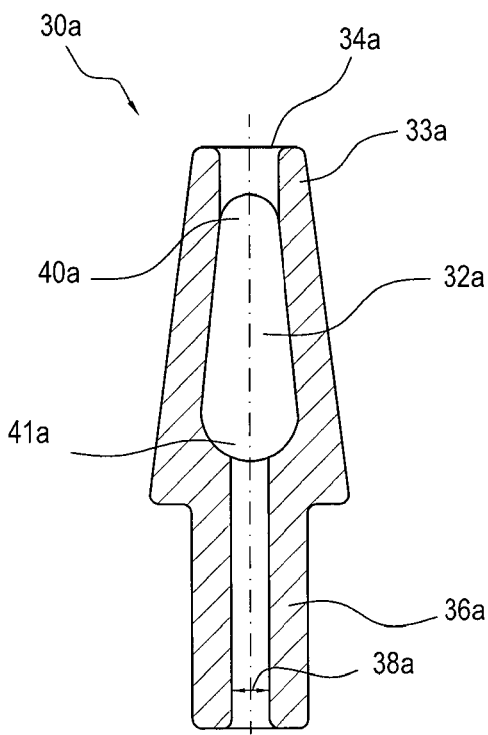
FIGS. 5-8 illustrate an exemplary embodiment of an anchor tip.
Figure 6:
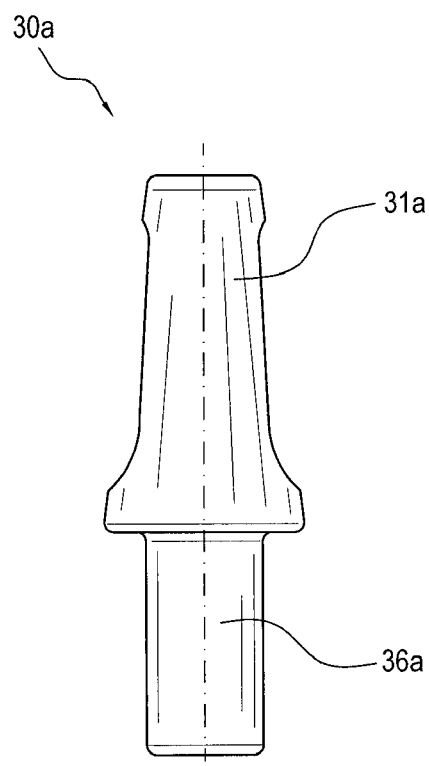
Figure 7:
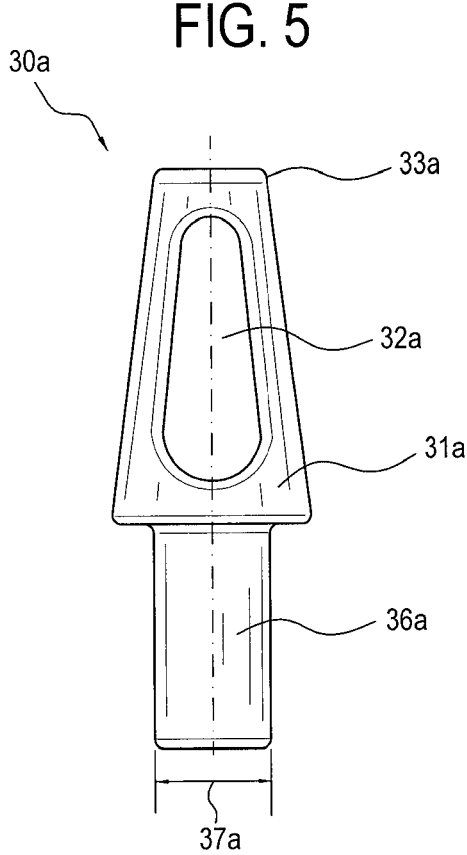
Figure 8:
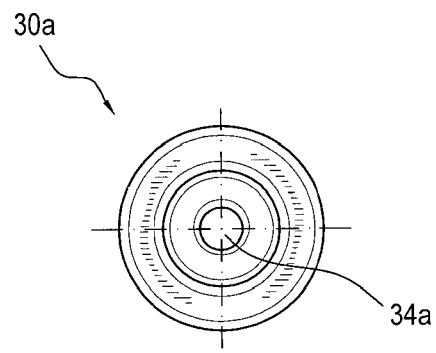

Tensionable construct 50 can be pre-loaded onto anchor tip 30 by tying static knot 60 on the outside of hole 34. Tensioning strand 52, tensionable loop 54, splice 55, and loop strands 56a and 56b pass through cannulated shaft 36 of anchor tip 30 and then through cannulated anchor body 20, exiting fixation device 10 at distal end 24 of anchor body 20. FIG. 4 illustrates loop strands 56a, 56b terminating into loop strand 56, and then loop strand 56 and tensioning strand 52 terminating into tensioning construct passing limb 58.

FIGS. 5-18 illustrate various exemplary embodiments 30a-30d of anchor tip 30.

FIGS. 5-8 illustrate exemplary embodiment 30a of anchor tip 30. Anchor tip 30a can include eyelet 32a, hole 34a, and cannulated shaft 36a. Hole 34a is positioned at the proximal tip of anchor tip 30a. Cannulated shaft 36a can have an outer width 37a and an inner width 38a, where inner width 38a represents how wide the hollow portion of cannulated shaft 36a is. In an exemplary embodiment, hole 34a can be wider than the inner width 38a. In another exemplary embodiment, hole 34a and inner width 38a can be approximately the same width. In another exemplary embodiment, hole 34a can be narrower than inner width 38a. Additionally, tip body 31a can be wider than outer width 37a of cannulated shaft 36a. Proximal end 33a of anchor tip 30a can be wider than, about as wide as, or narrower than, outer width 37a of cannulated shaft 36a. The size and shape of eyelet 32a can be any suitable size and shape. In the exemplary embodiment of FIGS. 5-8, eyelet 32a has two rounded ends, wherein first rounded end 40a, located near proximal end 33a of anchor tip 30a, is smaller than second rounded end 41a located near cannulated shaft 36a.

Figure 9:
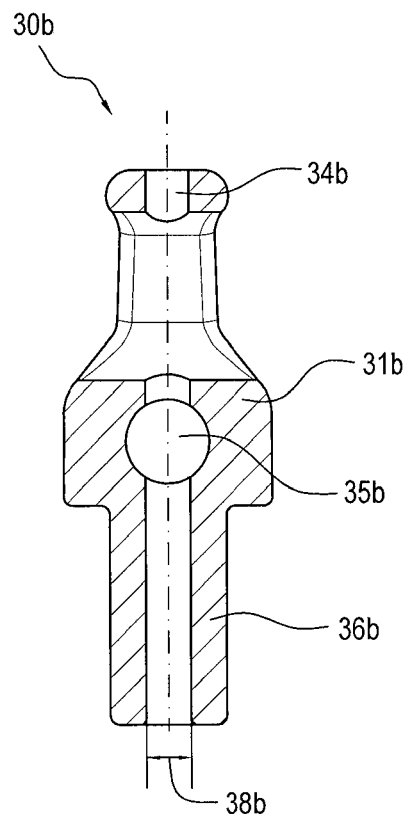
FIGS. 9-11 illustrate another exemplary embodiment of an anchor tip (a 3.5 mm round eyelet).
Figure 10:
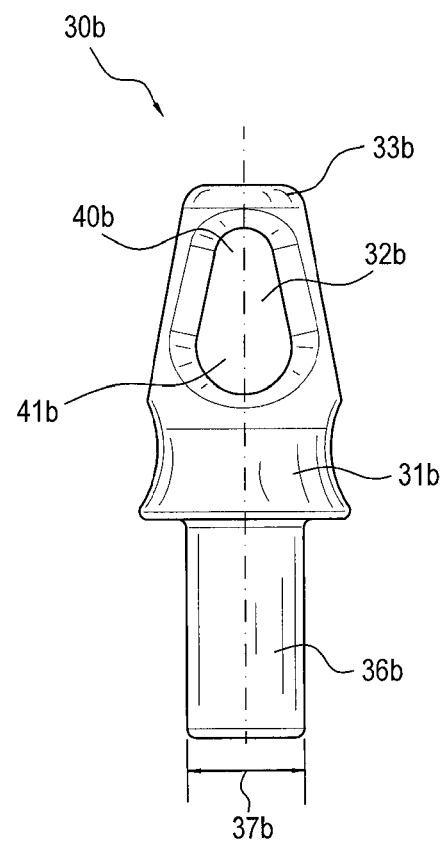
Figure 11:
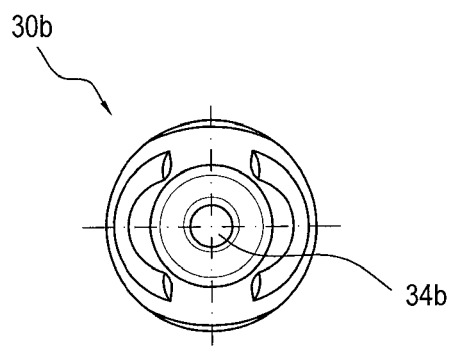

FIGS. 9-11 illustrate another exemplary embodiment 30b of anchor tip 30. Anchor tip 30b can include eyelet 32b, hole 34b, and cannulated shaft 36b. Hole 34b is positioned at positioned at the proximal tip of anchor tip 30b. Anchor tip 30b can further have a second hole 35b located on the side of anchor tip body 31b. Cannulated shaft 36b can have an outer width 37b and an inner width 38b, where inner width 38b represents how wide the hollow portion of cannulated shaft 36b is. In an exemplary embodiment, hole 34b can be wider than the inner width 38b. In another exemplary embodiment, hole 34b and inner width 38b can be approximately the same width. In another exemplary embodiment, hole 34b can be narrower than inner width 38b. Additionally, tip body 31b can be wider than outer width 37b of cannulated shaft 36b. Proximal end 33b of anchor tip 30b can be wider than, about as wide as, or narrower than outer width 37b of cannulated shaft 36b. The size and shape of eyelet 32b can be any suitable size and shape. In the exemplary embodiment of FIGS. 9-11, eyelet 32b has two rounded ends, wherein first rounded end 40b, located near proximal end 33b of anchor tip 30b, is smaller than second rounded end 41b located near cannulated shaft 36b.

Figure 12:
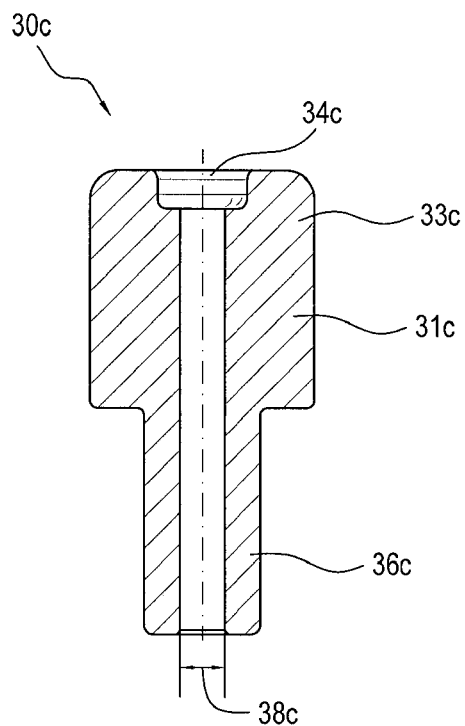
FIGS. 12-14 illustrate another exemplary embodiment of an anchor tip (a 4 mm round eyelet).
Figure 13:
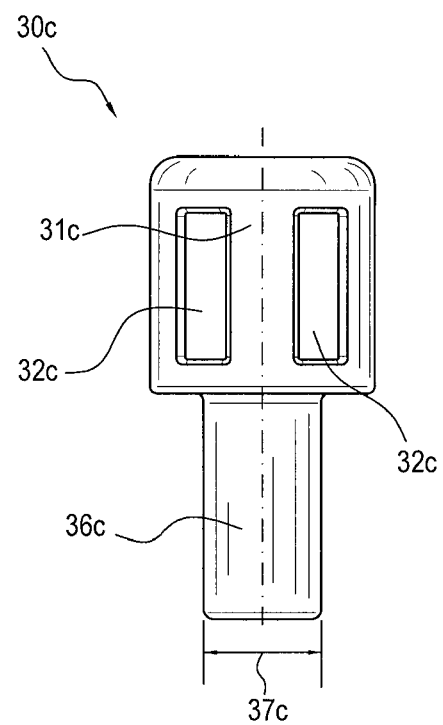
Figure 14:
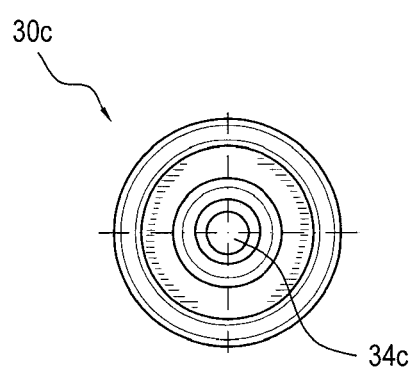
Figure 15:
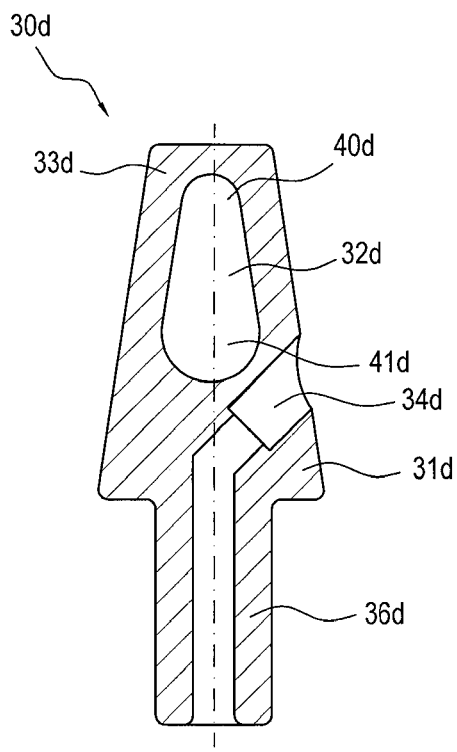
FIGS. 15-18 illustrate another exemplary embodiment of an anchor tip (an elongated open eyelet, curved).
Figure 16:
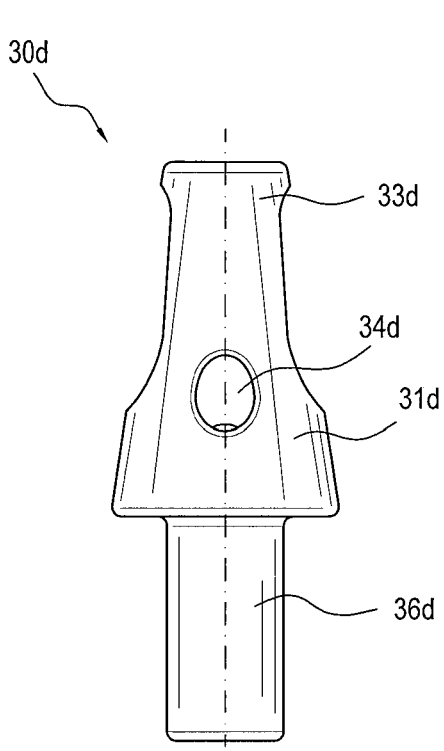
Figure 17:
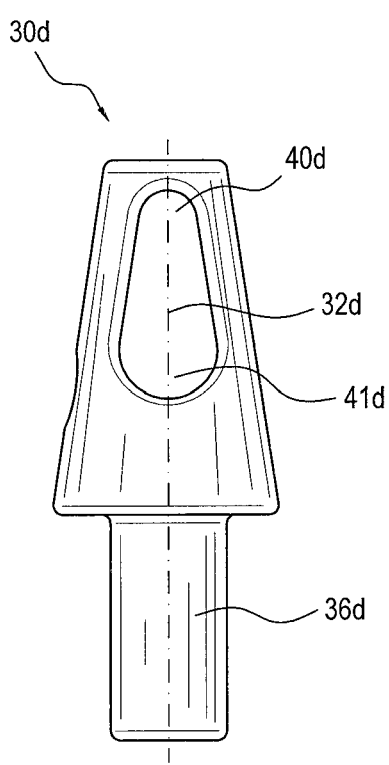
Figure 18:
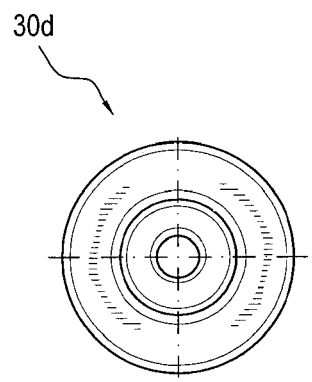
Figure 19A:
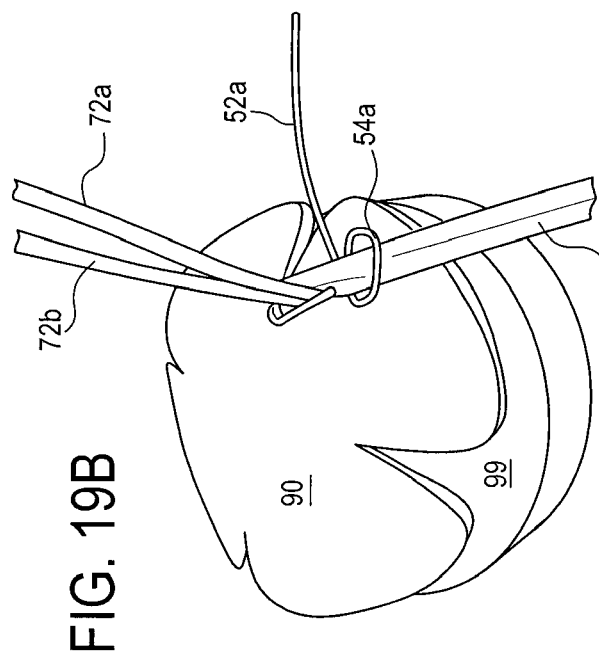
FIGS. 19A-D illustrate an exemplary embodiment of a surgical assembly.
Figure 19B:
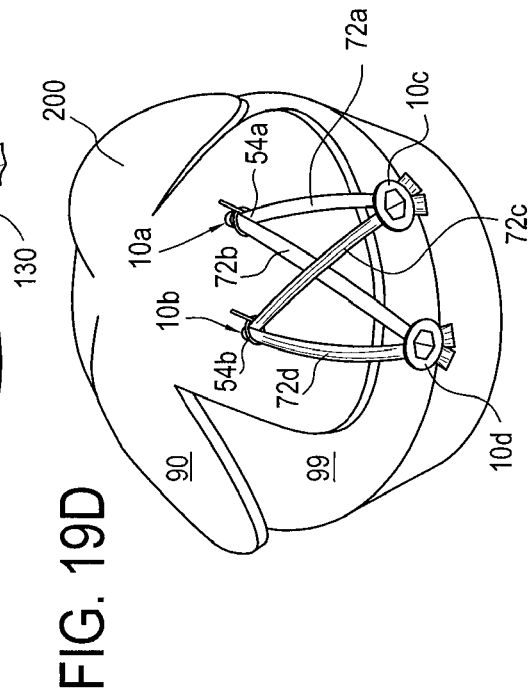
Figure 19C:
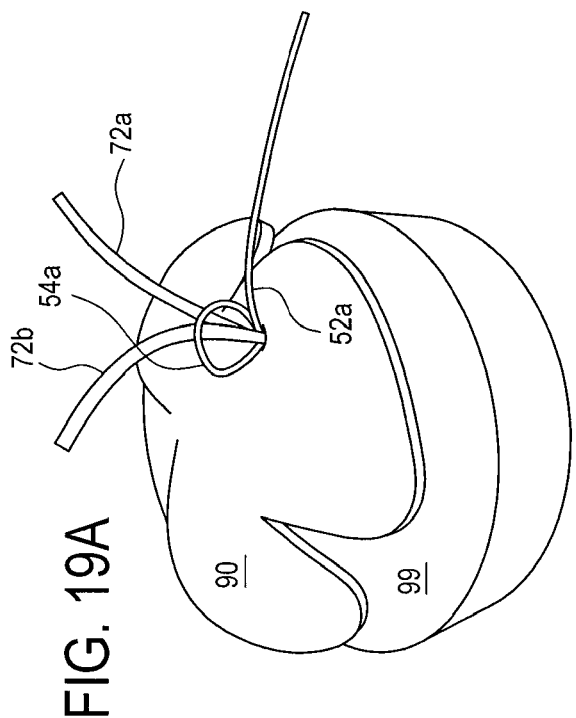
Figure 19D:
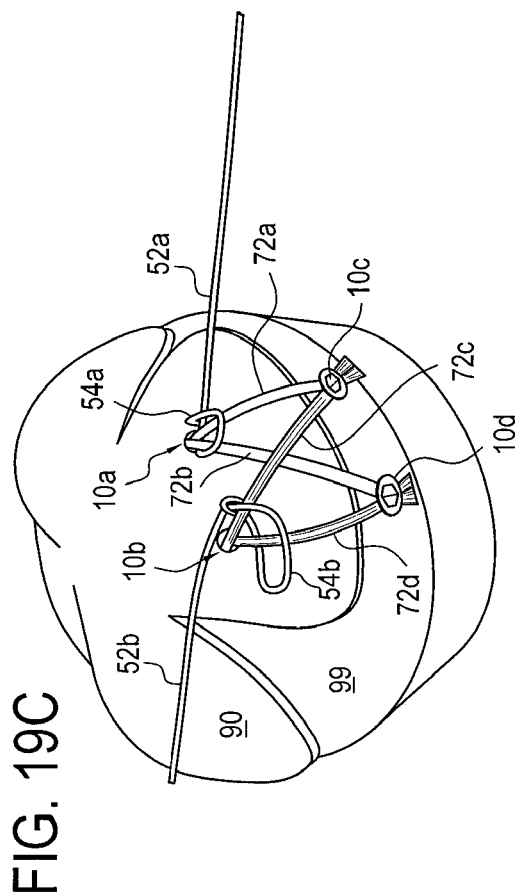

FIGS. 12-14 illustrate another example embodiment 30c of anchor tip 30. Anchor tip 30c can include eyelets 32c, hole 34c, and cannulated shaft 36c. Hole 34c is positioned at positioned at the proximal tip of anchor tip 30c. Cannulated shaft 36c can have an outer width 37c and an inner width 38c, where inner width 38c represents how wide the hollow portion of cannulated shaft 36c is. In an exemplary embodiment, hole 34c can be wider than the inner width 38c. In another exemplary embodiment, hole 34c and inner width 38c can be approximately the same width. In another exemplary embodiment, hole 34c can be narrower than inner width 38c. Additionally, tip body 31c can be wider than outer width 37c of cannulated shaft 36c. Proximal end 33c of anchor tip 30c can be wider than, about as wide as, or narrower than outer width 37c of cannulated shaft 36c. The size and shape of eyelets 32c can be any suitable size and shape. In the exemplary embodiment of FIGS. 12-14, eyelets 32c each have an approximately rectangular shape.

FIGS. 15-18 illustrate another exemplary embodiment 30d of anchor tip 30. Anchor tip 30d can include eyelet 32d, hole 34d, and cannulated shaft 36d. Hole 34d can be located on the side of anchor tip body 31d. Cannulated shaft 36d can have an outer width 37d and an inner width 38d, where inner width 38d represents how wide the hollow portion of cannulated shaft 36d is. Tip body 31d can be wider than outer width 37d of cannulated shaft 36d. Proximal end 33d of anchor tip 30d can be wider than, about as wide as, or narrower than outer width 37d of cannulated shaft 36d. The size and shape of eyelet 32d can be any suitable size and shape. In the exemplary embodiment of FIGS. 15-18, eyelet 32d has two rounded ends, wherein first rounded end 40d, located near proximal end 33d of anchor tip 30d, is smaller than second rounded end 41d located near cannulated shaft 36d.

FIGS. 19A-D illustrate simplified steps of an exemplary surgical tissue repair 100 with at least one exemplary fixation device described above. The exemplary surgical repair includes a medial row with first and second medial fixation devices 10a and 10b, and a lateral row with first and second lateral fixation devices 10c and 10d. First and second medial fixation devices 10a and 10b can be any embodiment of fixation device 10 described herein, and can comprise anchor body 20, anchor tip 30, tensionable construct 50, and flexible material 70.

First and second lateral fixation devices 10c and 10d can be any suitable knotless fixation devices known in the art. For example, first and second lateral fixation devices 10c and 10d can be any embodiment of fixation device 10 described herein, or any Arthrex SwiveLock® anchors (as disclosed and described in U.S. Pat. No. 8,012,174 issued Sep. 6, 2011, U.S. Pat. No. 9,005,246 issued Apr. 14, 2015, and US 2013/0296936 published Nov. 7, 2013, the disclosures of all of which are fully incorporated by reference in their entirety herein) or any Arthrex PushLock™ anchors (as described in U.S. Pat. No. 7,329,272 issued Feb. 12, 2008, the disclosure of which is fully incorporated herein by reference), or any combination of these devices.

First and second lateral fixation devices 10c and 10d do not have a tensioning construct or suture construct preloaded. Instead, first and second lateral fixation devices 10c and 10d are secured to the surgical assembly by limbs 72a, 72b, 72c, and 72d of flexible materials 70a and 70b. A first limb 72a of flexible material 70a and a first limb 72c of flexible material 70b are passed through an eyelet (not pictured) of first lateral fixation device 10c before the eyelet is loaded into a prepared bone tunnel or hole. Tension can be adjusted if necessary prior to advancing anchor body (not pictured) of lateral fixation device 10c into the prepared bone tunnel or hole. A second limb 72b of flexible material 70a and a second limb 72d of flexible material 70b are similarly passed through an eyelet (not pictured) of second lateral fixation device 10d before the eyelet is loaded into a prepared bone tunnel or hole. Tension can be adjusted if necessary prior to advancing anchor body (not pictured) of lateral fixation device 10d into the prepared bone tunnel or hole. First and second limbs 72a and 72b of flexible material 70a pass through tensionable loop 54a and thus can be tensioned by pulling tensioning strand 52a. Similarly, first and second limbs 72c and 72d of flexible material 70b pass through tensionable loop 54b and can be tensioned by pulling tensioning strand 52b. Thus, the final surgical assembly of repair 100 (FIG. 19D) having four fixation devices is secured by flexible materials 70a and 70b, while tensioning constructs 50a and 50b provide additional tensioning capabilities in addition to providing a backup knotless repair separate from the repair by flexible materials 70a and 70b.

Methods of soft tissue repair utilizing the surgical assemblies and devices described above are also disclosed. FIGS. 20-30 illustrate more detailed steps of an exemplary embodiment of a tissue repair method to achieve final repair 200 (FIG. 30).

FIG. 20 illustrates target tissue 90 and bone 99 with two prepared medial bone holes 111 and 112, with first tensionable knotless fixation device 10a implanted into prepared medial bone hole 111. Fixation device 10a has an anchor tip and anchor body (not visible since they have been implanted into prepared medial bone hole 111), tensionable construct 50a, and flexible material 70a. Tensionable construct has tensioning strand 52a, tensionable loop 54a, splice 55a, and loop strands 56a and 56b. Not pictured is the termination of the limbs into a single tensioning construct passing limb. Flexible material 70a has first limb 72a and second limb 72b. Not pictured is the termination of the limbs into a single flexible material passing limb. Tissue 90 may be soft tissue such as rotator cuff, for example.

Figure 21:
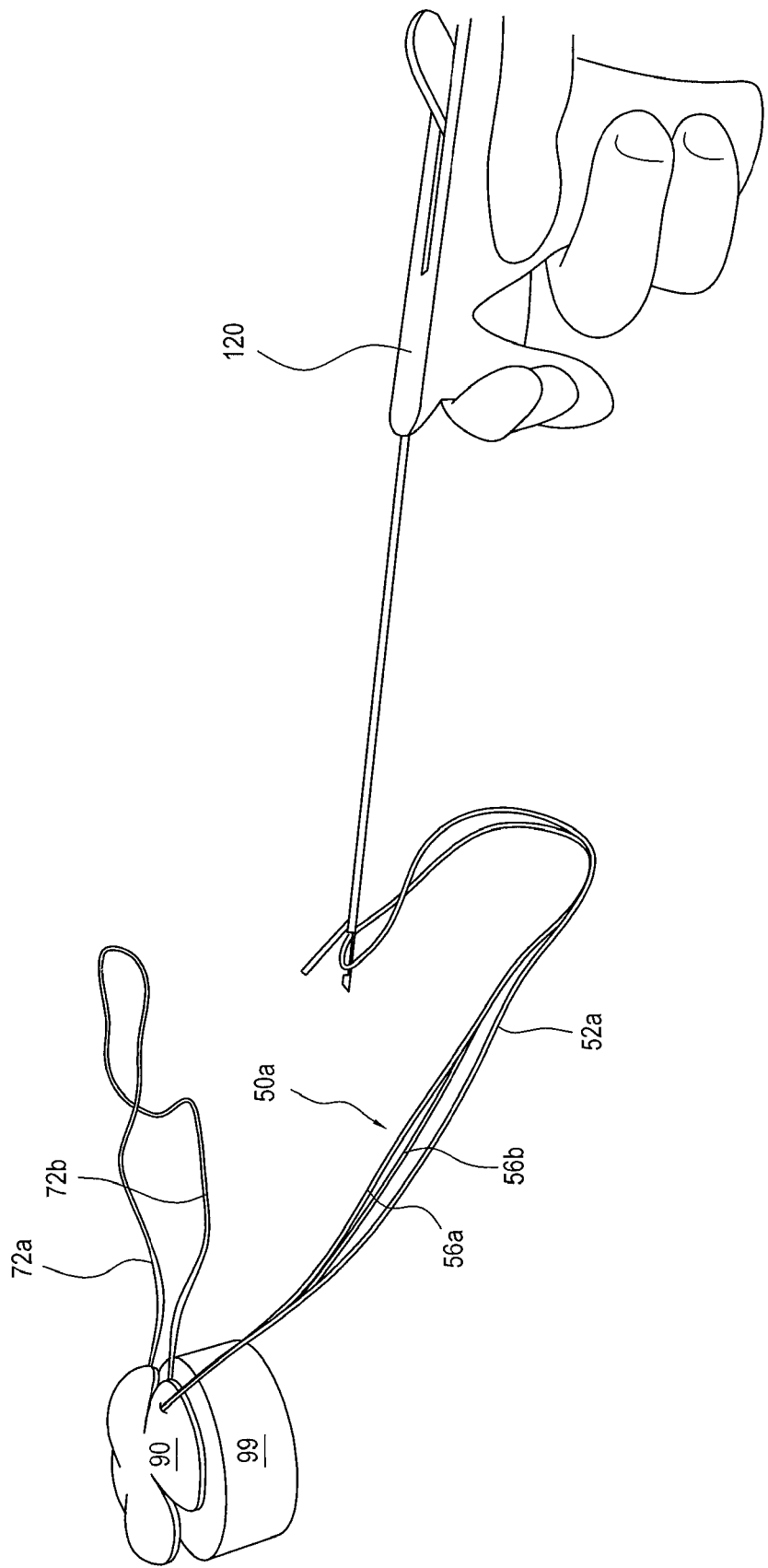

FIG. 21 illustrates the step of passing tensionable construct 50a through tissue 90 (for example, tendon, ligament, graft, etc.). In an exemplary embodiment, tensioning strand 52a and loop strands 56a and 56b terminate into a single tensioning construct passing limb 58a. Tensioning construct passing limb 58a is loaded into any suitable suture passer known in the art, for example the Arthrex Scorpion™ suture passer. Suture passer 120 is positioned in the desired location on the target tissue and tensioning construct passing limb 58a is passed through target tissue 90. In embodiments where tensioning strand 52a and loop strands 56a and 56b do not terminate into a single tensioning construct passing limb, then each strand may be passed separately, or loaded into a suture passer capable of passing multiple strands simultaneously.

Figure 22:
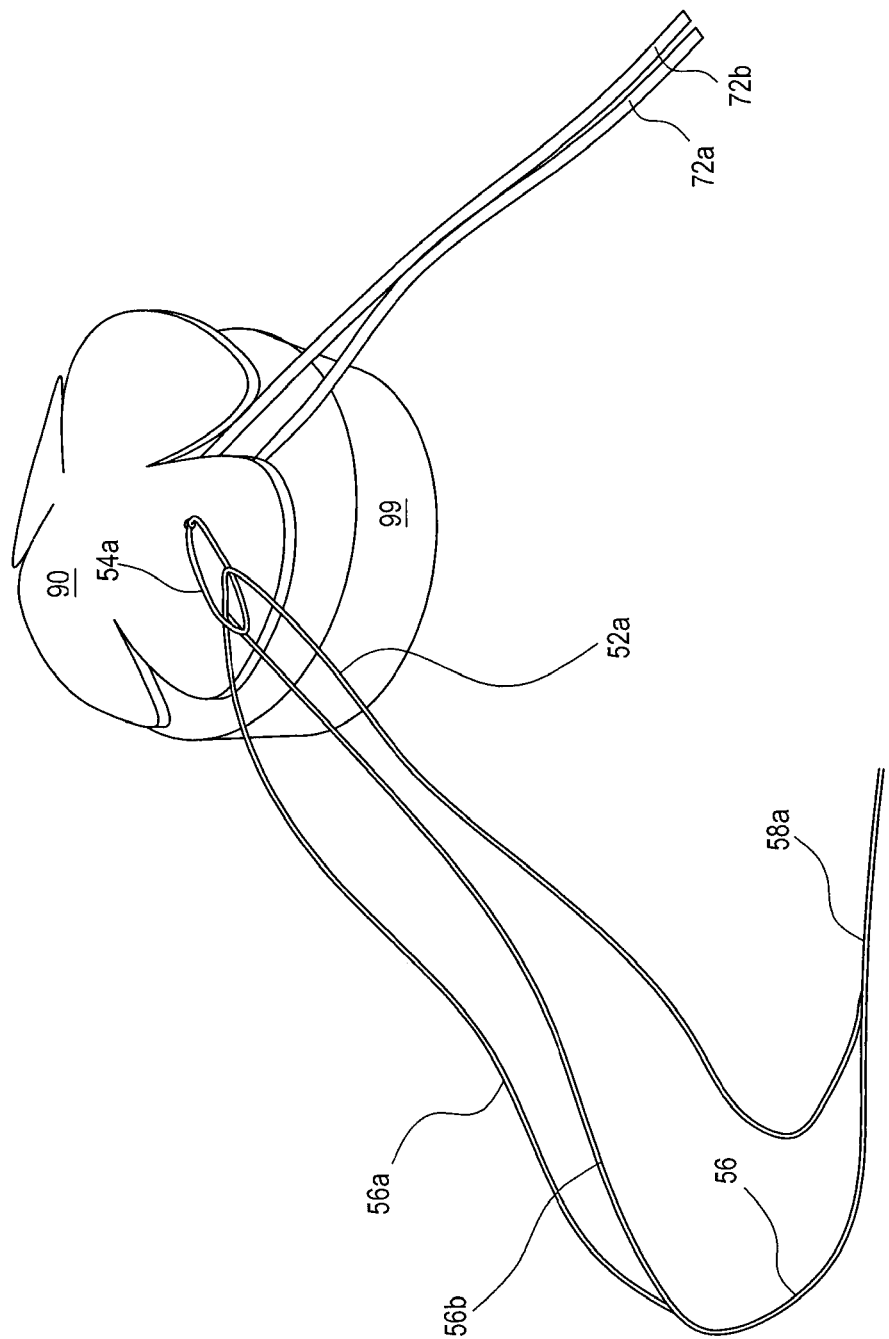

FIG. 22 illustrates tensioning construct passing limb 58a passed through target tissue 90. Tensioning construct passing limb 58a is pulled through target tissue such that tensioning strand 52a and tensionable loop 54a also pass through target tissue 90.

Figure 23:
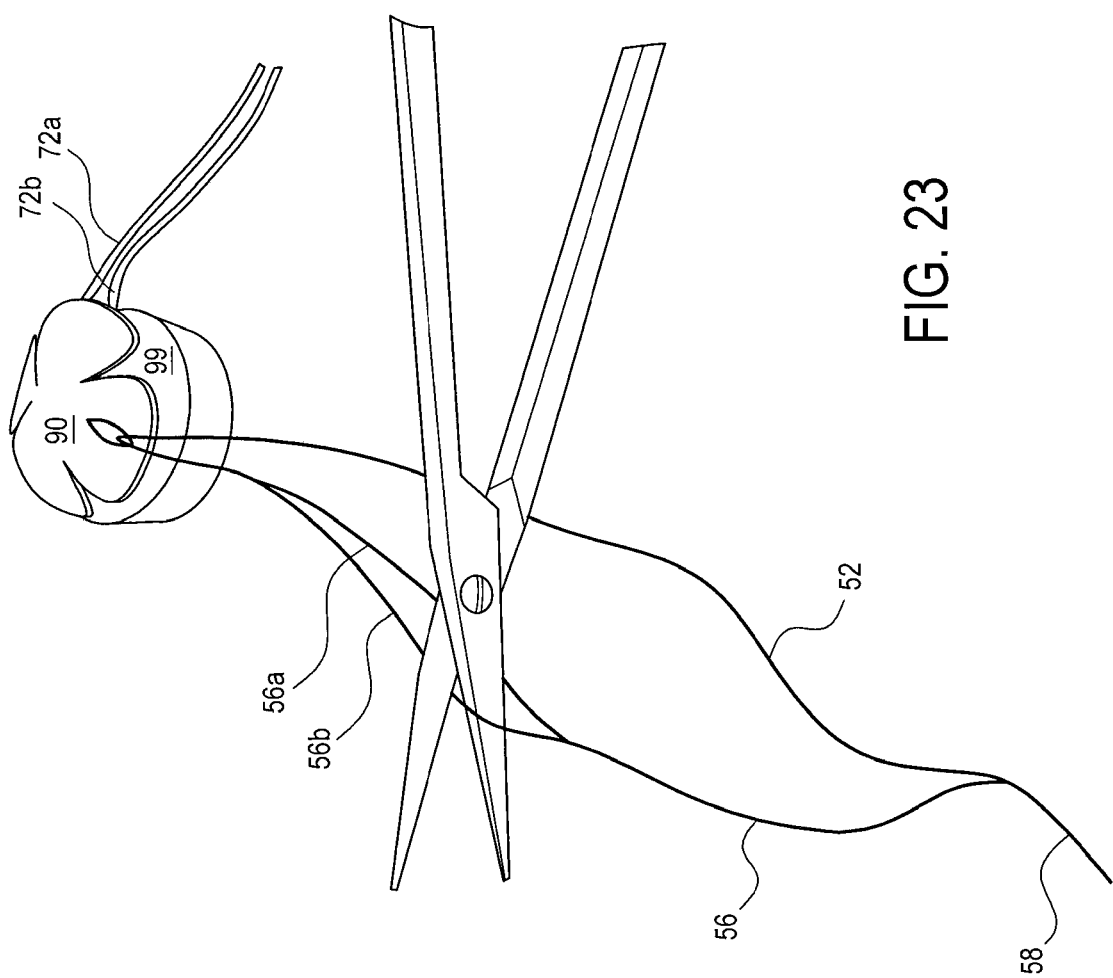
Figure 24:
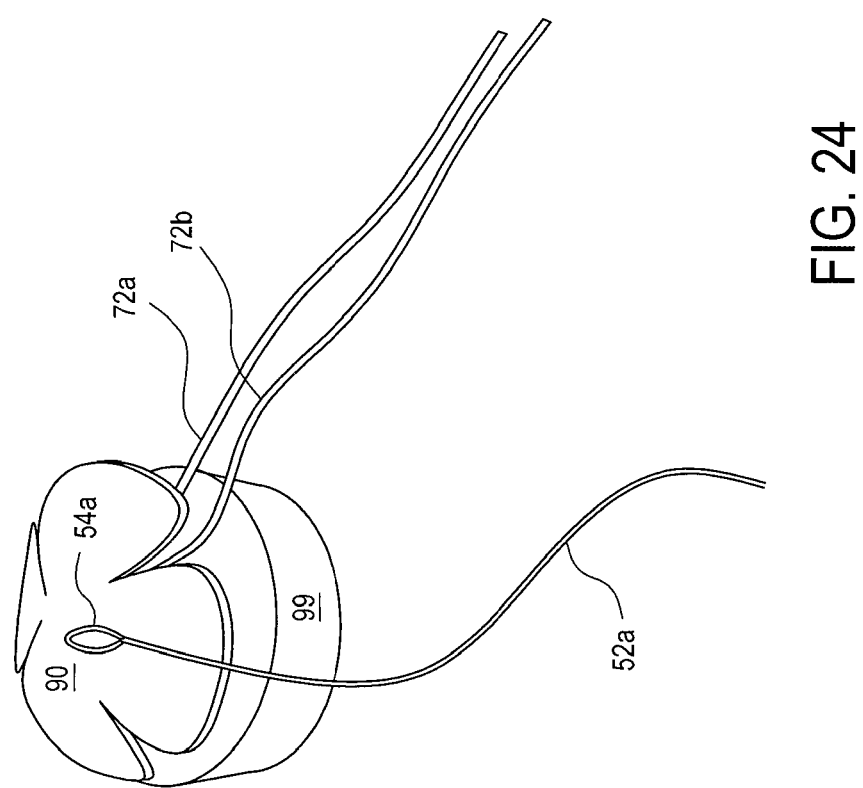

FIG. 23 illustrates the step of removing tensioning construct passing limb 58a from tensionable construct 50a. Cutting tensioning construct passing limb 58a leaves three strands: loop strands 56a, 56b, and tensioning strand 52a. Loop strands 56a and 56b wrap around tensionable loop 54a and may be discarded. FIG. 24 illustrates tensioning construct 50a with tensioning strand 52a and tensionable loop 54a passed through tissue 90, and loop strands 56a and 56b having been discarded. First and second limbs 72a and 72b of flexible material 70a have not yet been passed through tissue 90.

Figure 25:
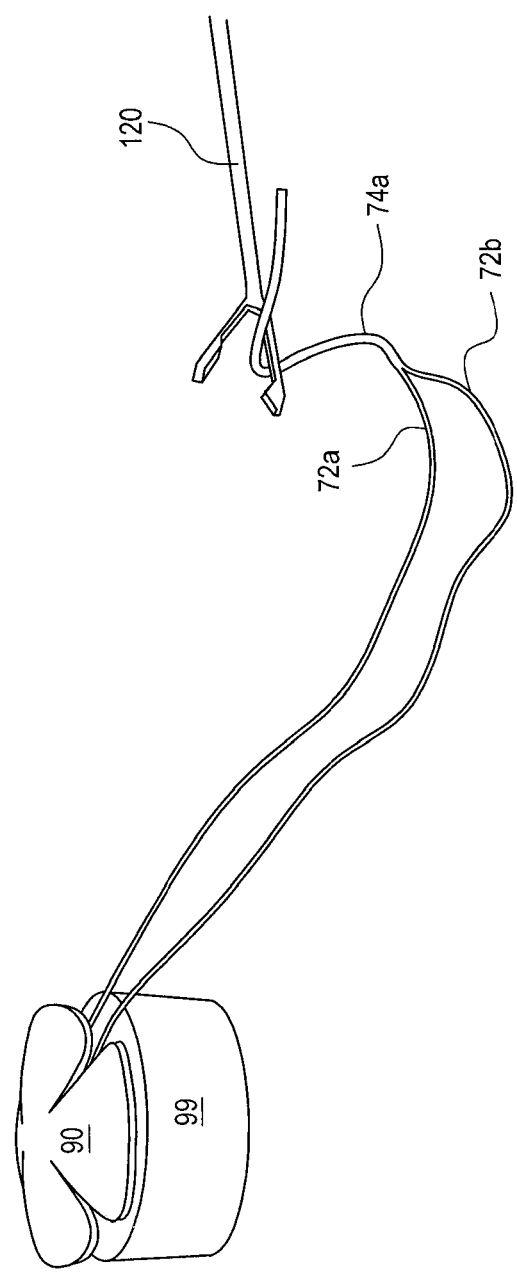

FIG. 25 illustrates the step of passing flexible material 70a through tissue 90. In an exemplary embodiment, first and second limbs 72a and 72b of flexible material 70a can terminate into a single flexible material passing limb 74a. Passing limb 74a is loaded into any suitable suture passer known in the art, for example the Arthrex Scorpion™ suture passer. Suture passer 120 is positioned at a location on the target tissue adjacent or near where tensioning construct 50a was passed, and passing limb 74a is passed through target tissue 90. In embodiments where first and second limbs 72a and 72b do not terminate into a passing limb, then each limb may be passed separately, or loaded into a suture passer capable of passing multiple limbs simultaneously.

Figure 26:
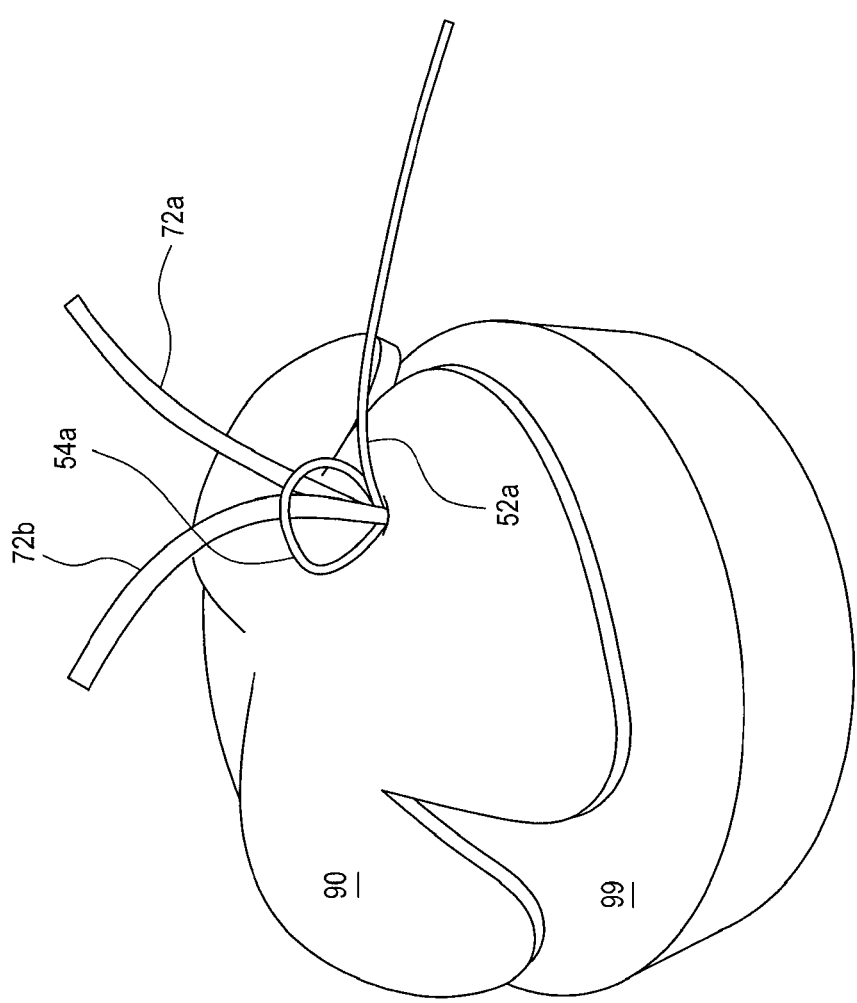

FIG. 26 illustrates tensioning strand 52a, tensionable loop 54a, and first and second limbs 72a and 72b all passed through tissue 90. Passing limb 74a has been cut and removed, leaving first and second limbs 72a and 72b separated.

Figure 27:
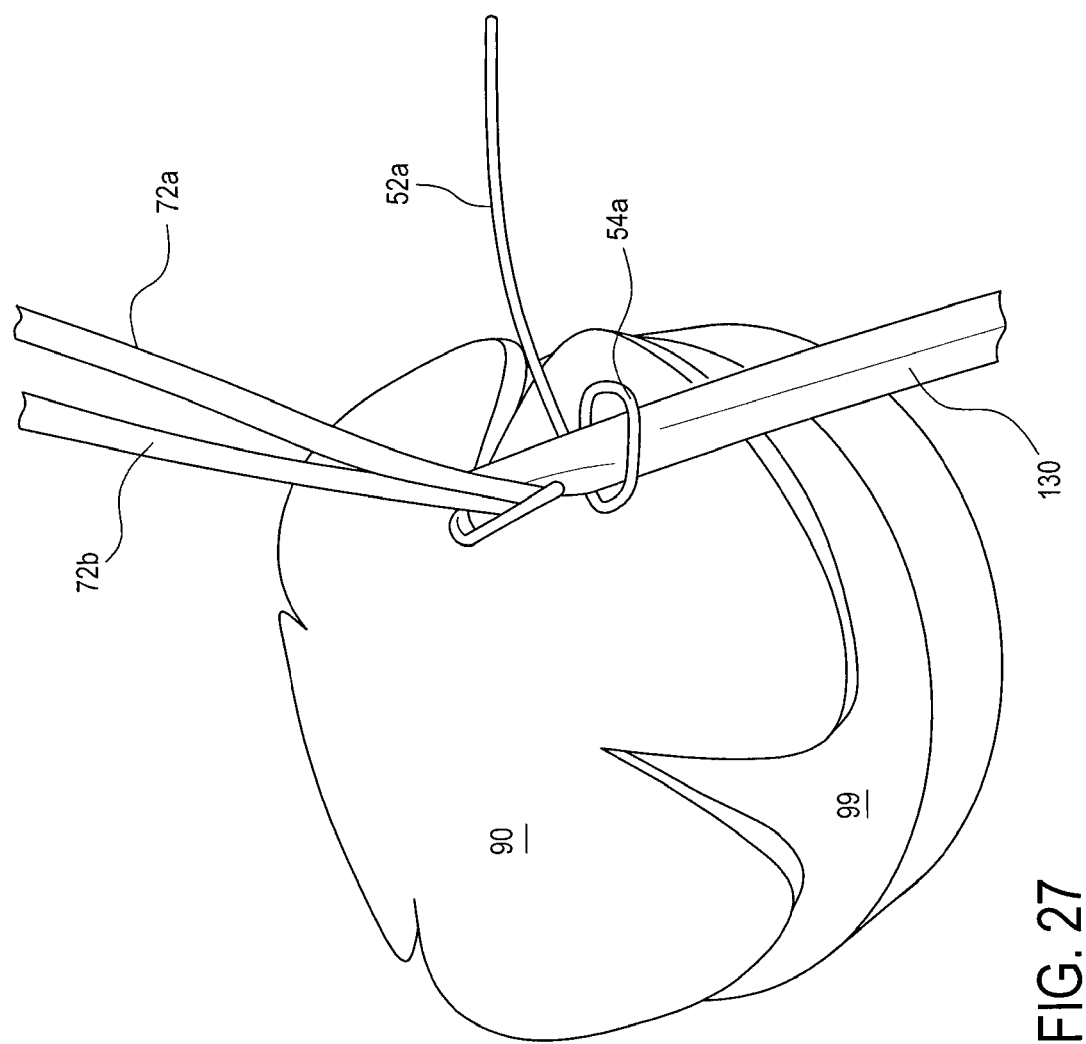

FIG. 27 illustrates the step of retrieving first and second limbs 72a and 72b through tensionable loop 54a. First and second limbs 72a and 72b can be retrieved using any retriever known in the art, for example the Arthrex FiberTape® Retriever. After being loaded into retriever 130, limbs 72a and 72b are pulled through tensionable loop 54a.

Figure 28:
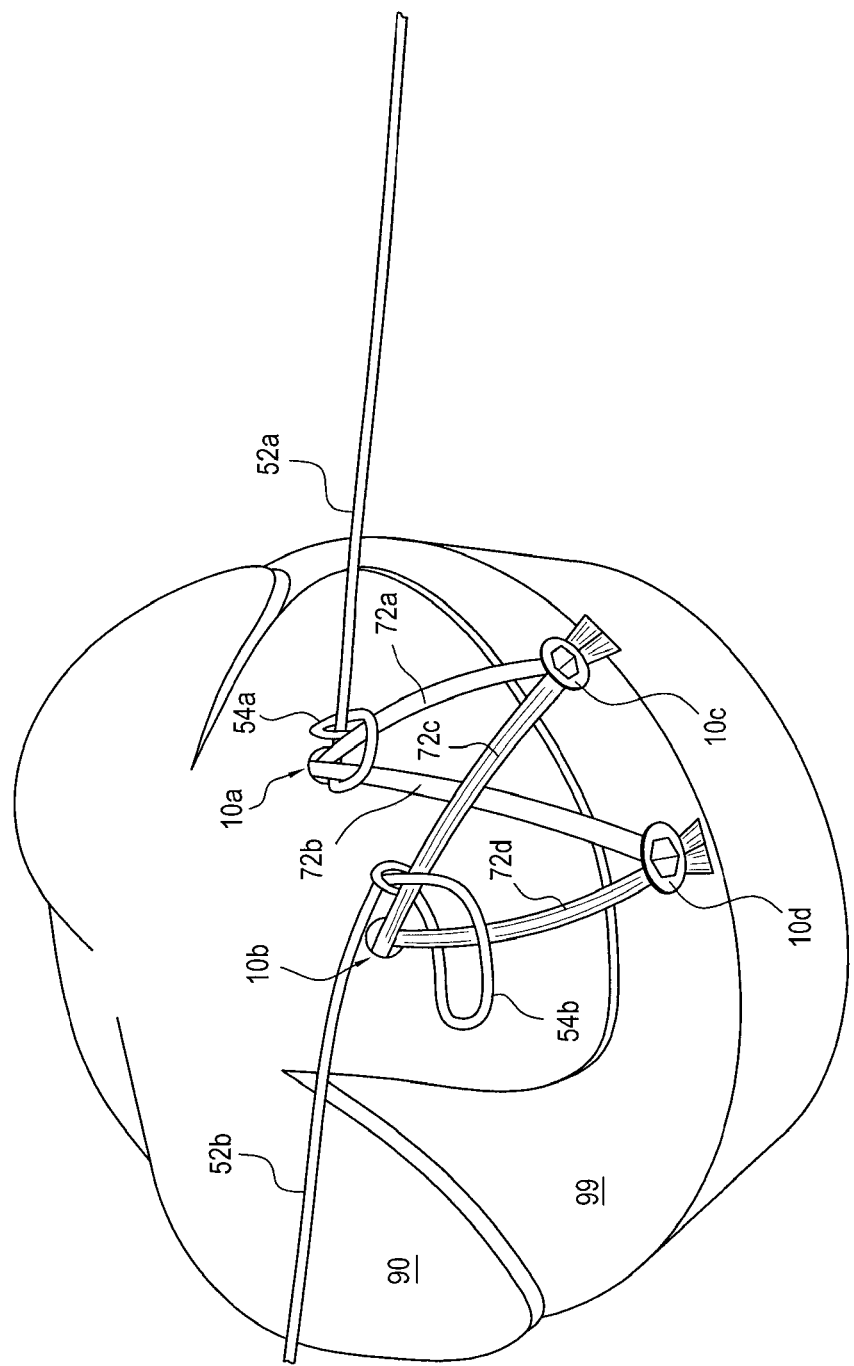

FIG. 28 illustrates the previously described steps having been repeated and completed for a second medial fixation device 10b. Second medial fixation device 10b has an anchor tip and anchor body (not visible since they have been implanted into prepared medial bone hole 112), tensionable construct 50b, and flexible material 70b. Tensionable construct has tensioning strand 52b, tensionable loop 54b, splice 55b, and loop strands (not pictured since they have already been discarded). Flexible material 70b has first limb 72c and second limb 72d.

Once first and second medial fixation devices 10a and 10b have been implanted, and tensioning strands 52a and 52b, tensionable loops 54a and 54b, splices 55a and 55b, and limbs 72a, 72b, 72c, and 72d have been passed through tissue 90, lateral bone holes can be prepared for first and second lateral fixation devices 10c and 10d. Lateral fixation devices 10c and 10d can be any suitable fixation devices, for example any embodiment of fixation device 10 described herein, or any Arthrex SwiveLock® anchors (as disclosed and described, for example, in U.S. Pat. No. 8,012,174 issued Sep. 6, 2011, U.S. Pat. No. 9,005,246 issued Apr. 14, 2015, and US 2013/0296936 published Nov. 7, 2013, the disclosures of all of which are fully incorporated by reference in their entirety herein), or any Arthrex PushLock™ anchors (as described in U.S. Pat. No. 7,329,272 issued Feb. 12, 2008, the disclosure of which is fully incorporated herein by reference), or any screw-in or push-in type anchors, or any combination of these devices.

First and second lateral fixation devices 10c and 10d do not have a tensionable construct or flexible material (suture tape) pre-loaded. Instead, first and second lateral fixation devices 10c and 10d are secured to the surgical assembly by limbs 72a, 72b, 72c, and 72d of flexible material 70a and 70b. First limb 72a of flexible material 70a and a first limb 72c of flexible material 70b are passed through an eyelet (not pictured) of first lateral fixation device 10c before the eyelet is loaded into a prepared bone hole. Tension can be adjusted if necessary prior to advancing anchor body (not pictured) of lateral fixation device 10c into the prepared bone hole. Second limb 72b of flexible material 70a and a second limb 72d of flexible material 70b are similarly passed through an eyelet (not pictured) of the second lateral fixation device 10d before the eyelet is loaded into a prepared bone hole. Tension can be adjusted if necessary prior to advancing anchor body (not pictured) of lateral fixation device 10d into the prepared bone hole.

After first and second lateral fixation devices 10c and 10d have been fixated/inserted/implanted, the resulting surgical assembly is shown in FIG. 28. Any remainder of limbs 72a, 72b, 72c, and 72d extending out from lateral fixation devices 10c and 10d may be cut off using any suitable suture cutter, for example the Arthrex FiberWire® cutter. FIG. 28 also illustrates the step of pulling tensioning strand 52a to tighten tensionable loop 54a in order to apply tension to first and second limbs 72a and 72b.

Figure 29:
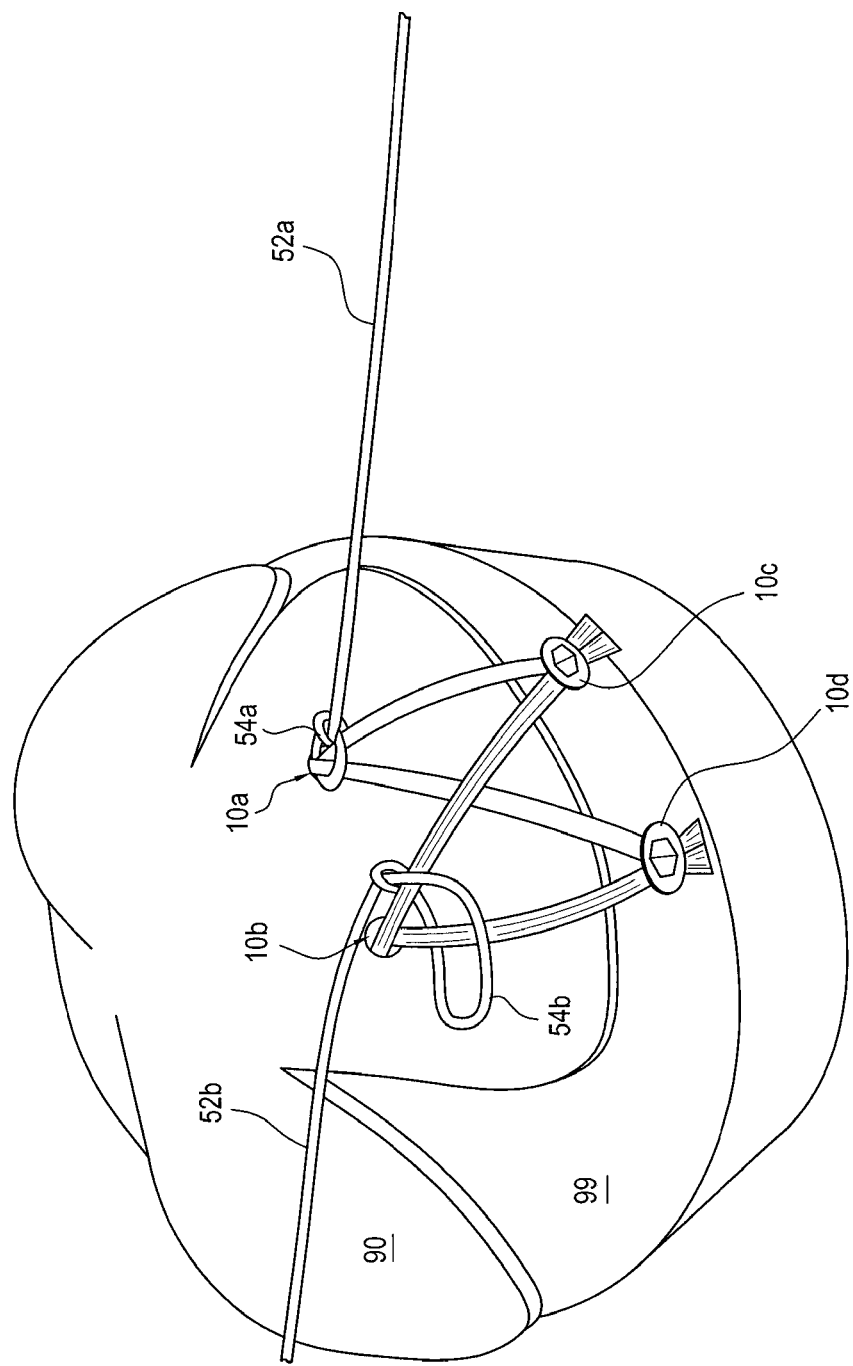
Figure 30:
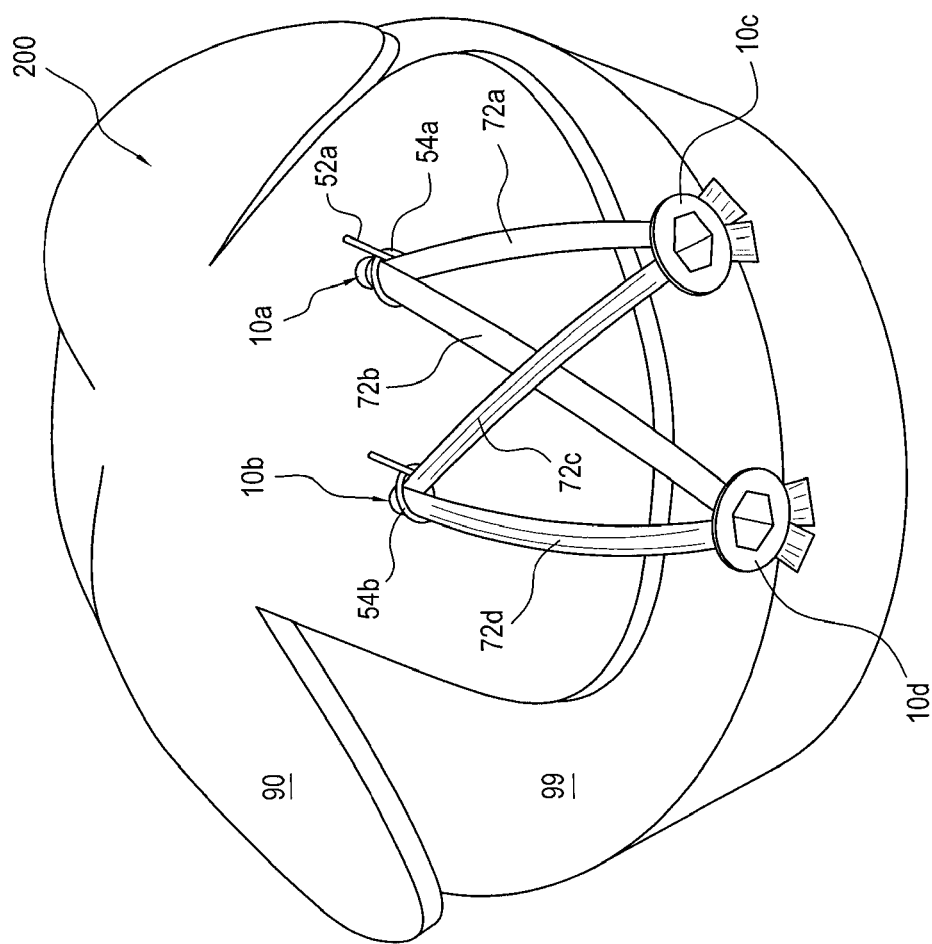

FIG. 29 illustrates the step of pulling tensioning strand 52b to tighten tensionable loop 54b in order to apply tension to first and second limbs 72c and 72d of suture construct 70b.

FIG. 30 illustrates the final surgical repair 200. Tensionable loops 54a and 54b have been tensioned, and tensioning strands 52a and 52b have been cut to remove them from the final assembly. Tensioning strands 52a and 52b can be cut using any suitable suture cutter, for example the Arthrex FiberWire® cutter.

An exemplary method of tissue repair comprises inter alia the steps of: (i) inserting into bone a surgical assembly comprising a fixation device; a tensionable construct pre-loaded on the fixation device, the tensionable construct including a tensioning strand, a knotless, adjustable, self-cinching, tensionable loop having an adjustable perimeter, and a splice adjacent the loop; and a flexible material (for example, suture tape) attached to the fixation device; and (ii) passing the tensionable construct and limbs of the flexible material around or through tissue to be fixated (or reattached) to bone, so that the tensionable loop is positioned over the tissue, and then passing limbs of the flexible material through the tensionable loop. The method may further comprise the step of securing the limbs of the flexible material into bone. The limbs may be secured with at least another fixation device that is inserted into bone. The method may further comprise the step of pulling on the tensioning strand to appropriate tissue to bone. The tissue may be soft tissue such as tendon, ligament, or graft.

Another exemplary method of soft tissue repair comprises inter alia the steps of: (i) inserting into bone a surgical assembly comprising a fixation device; a tensionable construct pre-loaded on the fixation device, the tensionable construct including a tensioning strand, a knotless, adjustable, self-cinching, tensionable loop having an adjustable perimeter, and a splice adjacent the loop; and a flexible material (for example, suture tape) attached to the fixation device; (ii) passing the tensionable construct and limbs of the flexible material around or through tissue to be fixated (or reattached) to bone so that the tensionable loop is positioned above and over the soft tissue, and above and over the bone; (iii) subsequently, passing limbs of the flexible material through the tensionable loop; and (iv) passing the limbs of the flexible material over the tissue and securing the limbs with additional fixation devices into bone, to form a mattress stitch repair.

Another exemplary method of soft tissue repair comprises inter alia the steps of: (i) inserting into bone a plurality of surgical assemblies, each surgical assembly comprising a fixation device; a tensionable construct pre-loaded on the fixation device, the tensionable construct including a tensioning strand, a knotless, adjustable, self-cinching, closed, tensionable loop having an adjustable perimeter, and a splice adjacent the loop; and a flexible material (for example, suture or suture tape) attached to the fixation device; (ii) passing the tensionable construct and limbs of the flexible material—of each surgical assembly—around or through tissue to be fixated (or reattached) to bone, so that the tensionable loop of each surgical assembly is positioned over and above the soft tissue, and over and above the bone; (iii) subsequently, passing limbs of the flexible material of each surgical assembly through the corresponding tensionable loop; and (iv) passing the limbs of each surgical assembly over the tissue, and securing the limbs with a plurality of fixation devices into bone, to form a mattress stitch repair.

The flexible strands and materials described above may be formed of strands of high strength suture material with surgically-useful qualities, including knot tie down characteristics and handling, such as Arthrex FiberWire® suture disclosed in U.S. Pat. No. 6,716,234, the disclosure of which is incorporated by reference in its entirety herein. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material. The flexible strand may be a high-strength suture, such as an ultrahigh molecular weight polyethylene (UHMWPE) suture which is the preferred material as this material allows easy splicing.

The suture constructs may be formed of optional colored strands, such as black or blue, to assist surgeons in distinguishing between suture lengths with the trace and suture lengths without the trace. Preferably, each of the limbs may be provided in different colors to assist surgeons in retrieving one limb from each of the knotless fixation devices and then loading them through another knotless fixation device, during the formation of the crisscross suturing pattern.

Suture constructs may be coated (partially or totally) with wax (beeswax, petroleum wax, polyethylene wax, or others), silicone, silicone rubbers, PTFE (Teflon, Hostaflon, or others), PBA (polybutylate acid), ethyl cellulose (Filodel) or other coatings, to improve lubricity of the suture or tape, knot security, pliability, handleability, or abrasion resistance, for example.

Suture constructs may also contain a bioabsorbable material, such as PLLA or one of the other polylactides, for example, and/or may be formed of twisted fibers having strands of a contrasting color added to the braided threads, to make the suture more visible during surgical procedures. The colored strands can be dyed filaments or strands, for example.

The surgical assembly and methods of the present invention have applicability to tissue repairs such as rotator cuff repair, Achilles tendon repair, patellar tendon repair, knee repairs such as ACL and/or PCL reconstruction, hip and shoulder reconstruction procedures, and applications involving repairing soft tissue to bone.

Figure 31A:
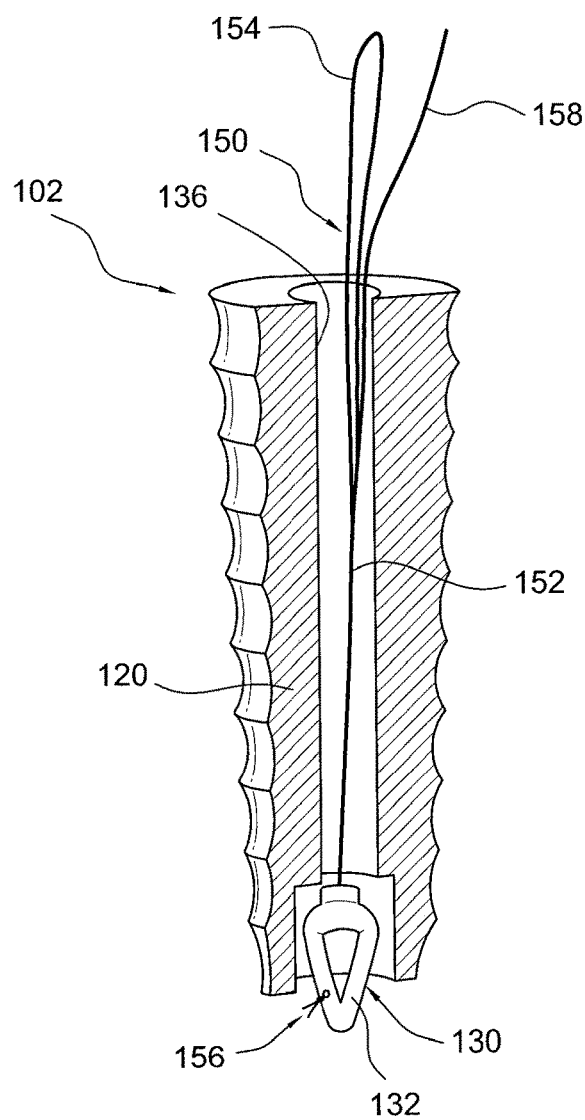
FIGS. 31A-B illustrate pre-looped and non-pre-looped tensionable fixation devices in accordance with an exemplary embodiment of the present invention.
Figure 31B:
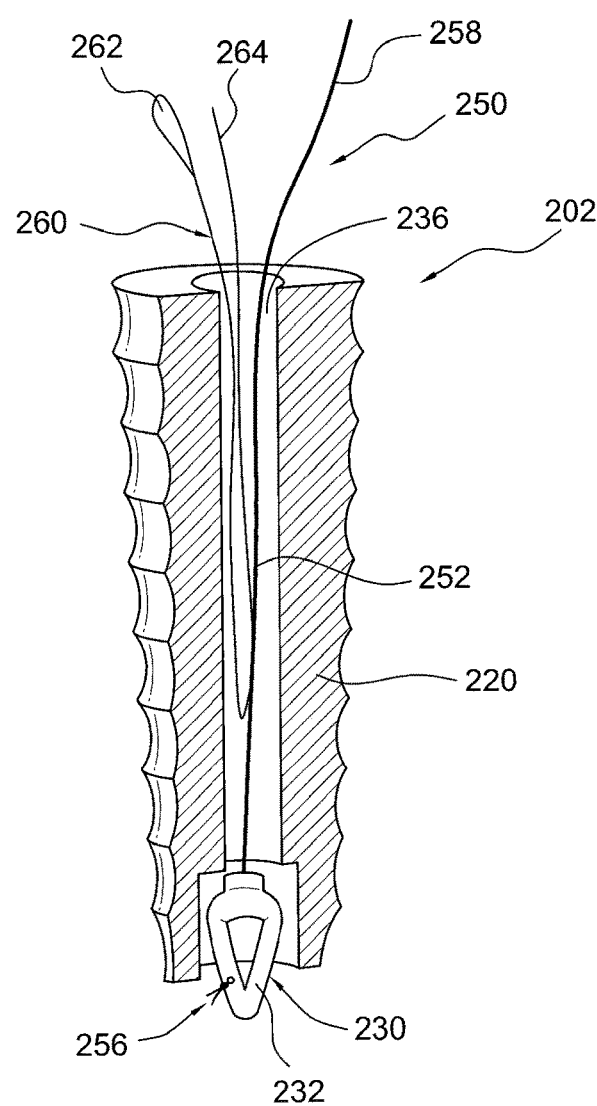

FIG. 31A illustrates a tensionable fixation device 102 with a pre-loaded tensionable loop (pre-looped tensionable fixation devices), and FIG. 31B illustrates another type of tensionable fixation device without a pre-loaded tensionable loop (non-pre-looped tensionable fixation device) 202 used in methods of tissue repair illustrated in FIGS. 32A-32D, FIGS. 33A-33C, and FIGS. 34A and 34B, in accordance with various exemplary embodiments as disclosed. The methods of FIGS. 32A-32D, 33A-33C, and 34A and 34B are more secure than conventional knot repairs, are faster than conventional repairs thus saving time and money in the OR, eliminate the potential of knots impinging against adjacent structures and causing irritation or damage, and eliminate any knot failures of the repair.

Figure 33A:
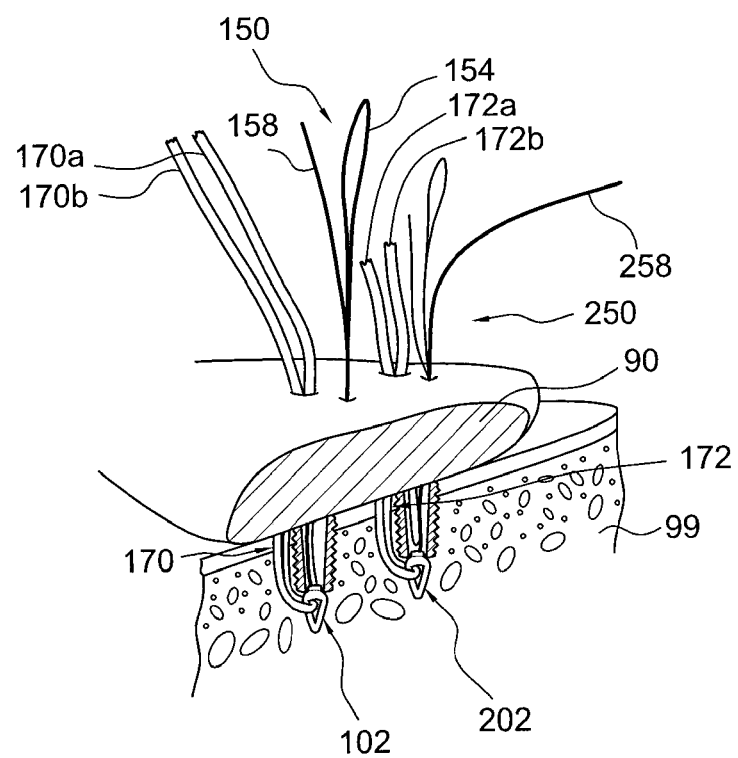
FIGS. 33A-33C illustrate another exemplary method of tissue repair using the fixation devices of FIGS. 31A-B.

As seen in FIG. 31A, the pre-looped tensionable suture anchor fixation device 102 that preferably includes an anchor body 120 that receives an anchor tip 130. The anchor tip 130 preferably includes an eyelet body 132 having an eyelet 160 sized to receive a flexible member 170 (FIG. 33A). The tensionable pre-looped suture anchor fixation device 102 supports a tensionable construct 150 in a shaft 136 of the anchor body 120. The tensionable pre-looped suture 150 may include a flexible strand 152 and a pre-looped tensionable loop 154 spliced through a flexible strand 152. The flexible strand 152 may have a knotted end 156 that engages the eyelet body 132 of the anchor tip 130 to prevent the strand 152 from pulling through the anchor body 120, and a free end 158 opposite the knotted end 156. Both the free end 158 and at least a portion of the tensionable loop 154 extend outside of the fixation device 102.

As seen in FIG. 31B, the non-pre-looped tensionable suture anchor fixation device 202 may include an anchor body 220 and an anchor tip 230 (having an anchor tip body 232 and knotted end 256), similar to pre-looped tensionable fixation device 102. The anchor tip 230 may include an eyelet body 232 having an eyelet 160 sized to receive a flexible member 172 (FIG. 33A). The non-pre-looped tensionable suture anchor fixation device 202 supports a non-pre-looped tensionable construct 250 in a shaft 236 within the anchor body 220. The non-pre-looped tensionable suture construct 250 may include a flexible strand 252 that has a knotted end 256 engaging the eyelet body 232 of the anchor tip 230, and an opposite free end 258. The flexible strand 252 is preferably coupled with a passer device 260. The passer device 260 may be any known suture shuttling or puller that includes an eyelet 262 and a tail end 264 opposite the eyelet 262. The passer device 260 may be threaded through a splice in the flexible strand 252. The free end 258 of the flexible strand 252 and both the eyelet 262 and tail end 264 of the passer device 260 are outside of the anchor body 220.

Figure 32D:
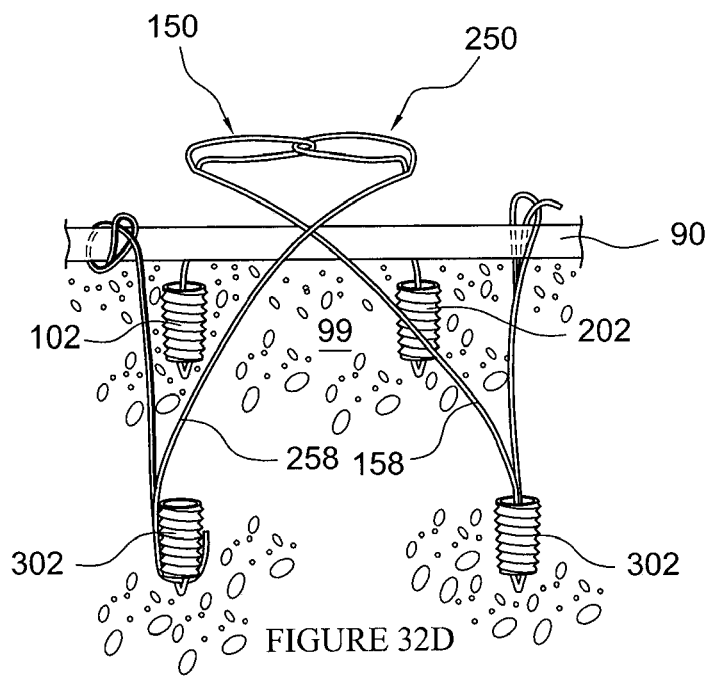

FIGS. 32A-32D illustrate an exemplary method of tissue repair using the pre-looped and non-pre-looped tensionable fixation devices 102 and 202 of FIGS. 31A and 31B, respectively. As seen in FIG. 32A, the pre-looped and non-pre-looped tensionable fixation devices 102 and 202 are preferably pre-loaded with constructs 150 and 250, respectively, and are anchored in bone 99, preferably in a medial row. The tensionable construct 150 of the pre-looped tensionable fixation device 102 is passed through a target area in the tissue 90 (soft tissue layer). The construct 250 of the non-pre-looped tensionable fixation device 202 is passed through another target area in the tissue 90. Once passed through the tissue 90, the pre-looped tensionable loop 154 (or a portion thereof) and the free end 158 of the pre-looped tensionable construct 150, and the free end 258, the passer device eyelet 262 and tail end 264 of the non-pre-looped tensionable construct 250, are above or outside of the tissue 90. A cannula 300 may be optionally provided to facilitate management of the constructs 150 and 250.

Once the constructs 150 and 250 are passed through the tissue 90, interlocking loops are formed by first threading the free end 258 of the non-pre-looped tensionable construct 250 through the tensionable loop 154 of the tensionable pre-threaded construct 150 and then threading the free end 258 back through the eyelet 262 of the passer device 260 of the non-pre-threaded tensionable construct 250, as seen in FIG. 32B. The tail end 264 of the passer device 260 can then be pulled away from the repair to thread the free end 258 of the strand 252 through itself (as shown by arrows in FIG. 32B), thereby forming two interlocking loops, as seen in FIG. 32C. Those loops may then be tightened by pulling on the free ends 158 and 258, as seen in FIG. 32C, thereby providing a secure suture on the tissue repair.

FIG. 32D illustrates an optional step of further securing the free ends 158 and 258 of the constructs 120 and 250, respectively, once tightened on the repair, by employing additional fixation devices 302 to fix the free ends 158 and 258 to bone 99. The additional fixation devices 302 may be any known fixation device, such as SwivelLock suture anchors. Cinch-loop sutures (90) may be placed and fixed to the lateral row anchor to eliminate dog ears. The fixation devices 302 are preferably arranged in a lateral row so that the free ends 158 and 258 of the constructs 120 and 250 may cross one another and be secured via fixation devices 302 to form a suture bridge that links the medial row of suture anchors to the lateral row of suture anchors.

Figure 33B:
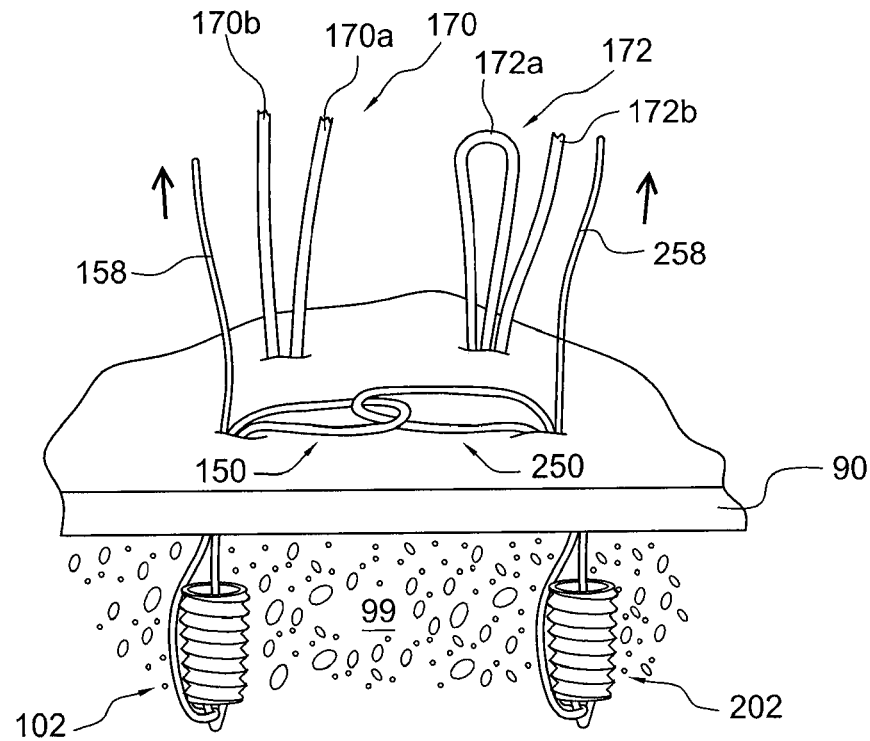
Figure 33C:
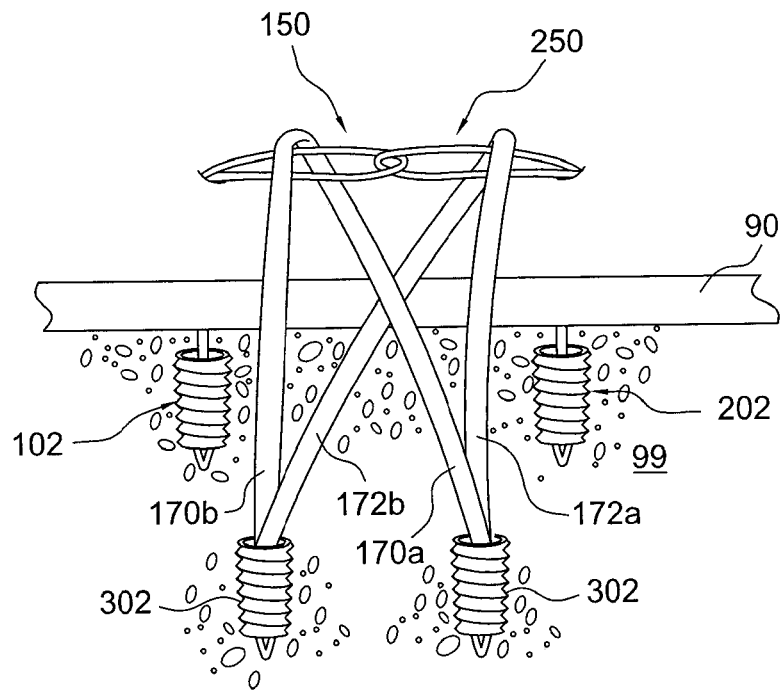

FIGS. 33A-33D illustrate another exemplary method of tissue repair using the tensionable and non-tensionable fixation devices 102 and 202 of FIG. 31 and incorporating flexible materials 170 and 172. As seen in FIG. 33A, once the fixation devices 102 and 202 are anchored to bone 99 and the constructs 150 and 250 are passed through the tissue 90, the limbs 170a and 170b of flexible material 170 may be passed through the tissue 90 proximal to the tensionable construct 150, and the limbs 172a and 172b of flexible material 172 may be passed through the tissue 90 proximal to the non-tensionable construct 250. As seen in FIG. 33B, two interlocking loops of the constructs 150 and 250 are formed in the same manner as disclosed above regarding the embodiment of FIGS. 32A-32D. The limbs 170a, 170b of flexible material 170 and limbs 172a, 172b of flexible material 172 may be passed through the tissue either before or after the interlocking loops of the constructs 150 and 250 are formed and are preferably passed through the tissue before the interlocking loops of the constructs 150 and 250 are fully tensioned or tightened. Once the interlocking loops of the constructs 150 and 250 are fully tensioned to form a load sharing rip-stop on the repair, the limbs 170a, 170b of flexible material 170 and limbs 172a, 172b of flexible material 172 may be pulled over the rip-stop of constructs 150 and 250 to be secured to additional fixation devices 302 anchored in bone 99. In this embodiment, the flexible materials 170 and 172, such as suture tape, act as the primary securing sutures for the tissue repair. The additional fixation devices 302 may be arranged in a lateral row in bone 99 and the limbs 170a, 170b of flexible material 170 and limbs 172a, 172b of flexible material 172 may cross one another to form a bridge to compress the underlying tissue against the bone. For example, the limb 170a and the limb 172a may be secured to one of the additional fixation devices 302 and the limb 170b and the limb 172b may be secured to the other of the additional fixation devices 302, as seen in FIG. 33C.

Figure 34A:
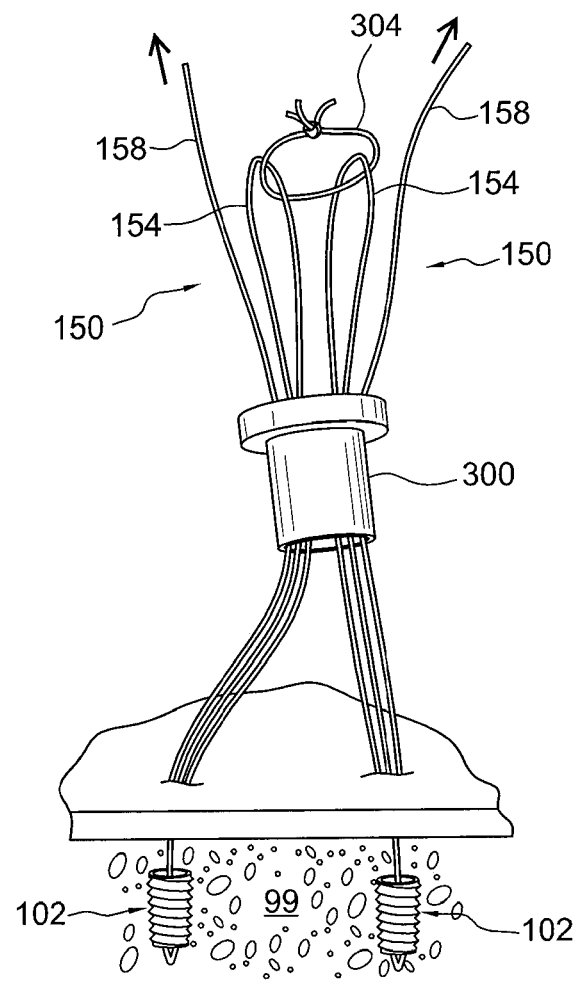
FIGS. 34A and 34B illustrate a further exemplary method of tissue repair with the tensionable fixation device of FIGS. 31A-B.
Figure 34B:
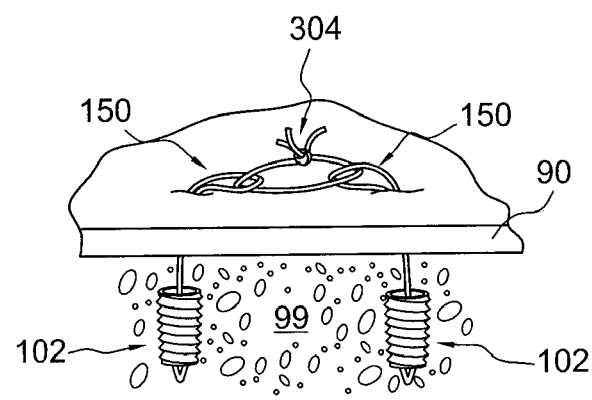

FIGS. 34A and 34B illustrate yet another exemplary method of tissue repair using two tensionable fixation devices 150. Unlike the embodiments of FIGS. 32A-32D and 33A-33C, the embodiment of FIGS. 34A and 34B do employ a tensionable fixation device. As seen in FIG. 34A, two of tensionable fixation devices 102 are preloaded with constructs 150 and anchored in bone 99 and the constructs 150 are passed through the tissue 90. The tensionable loops 154 of each construct 150 are passed separately though two different target areas in the tissue 90 and then tied together with a knotted segment 304. A cannula 300 may be used to facilitate management of the constructs 150 outside of the tissue 90. Once the loops 154 are tied together, they are brought down or over the tissue 90 by pulling on the free ends 158 and 258 of the tensionable constructs 150, as seen in FIG. 34B. The knotted segment 304 preferably remains in an open loop, thereby facilitating sliding of the interlinked loops 154 on each other as the loops are tensioned.

Figure 35:
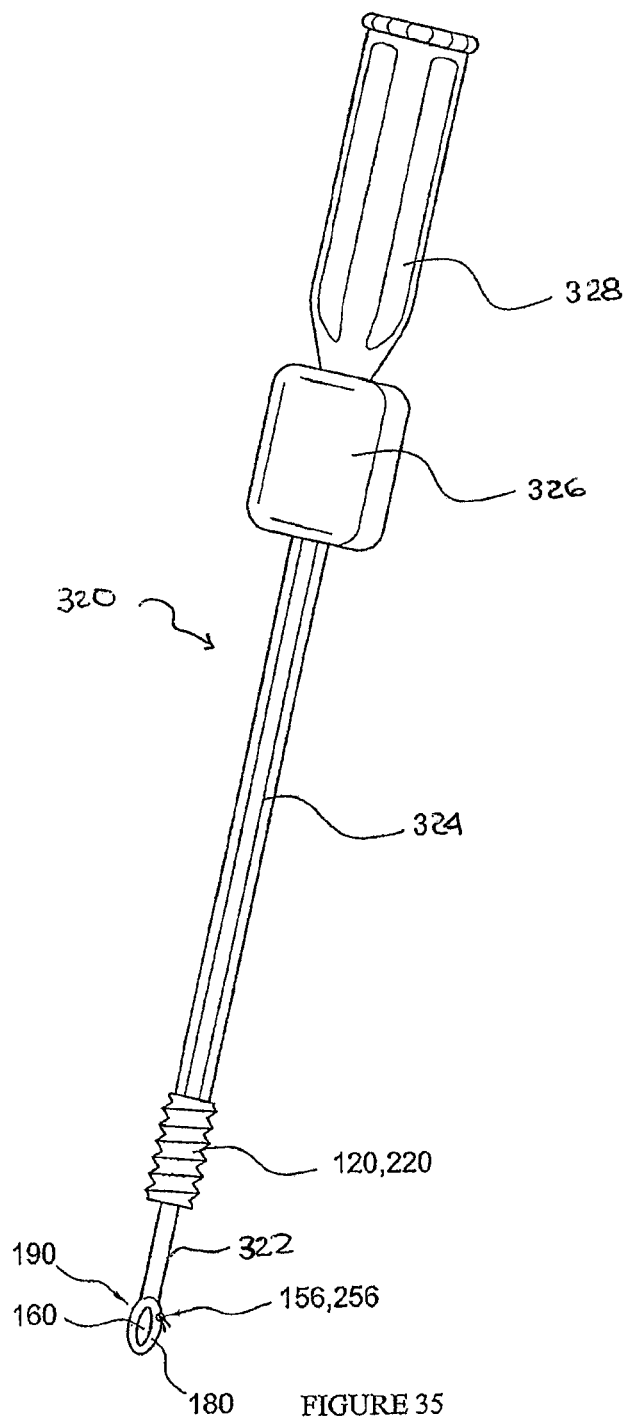
FIG. 35 illustrates a driver and anchor assembly.

FIG. 35 illustrates a driver and anchor assembly construct. The driver 320 may generally include a cannulated rod 322 and a reverse threaded sleeve 324. A thumb pad 326 can be located below a handle 328 of the driver and anchor assembly construct. Reverse threaded sleeve 324 serves to drive an anchor body 120, such as a screw-in anchor body (such as a SwiveLock anchor), into a solid surface, such as into a bone. Located on the eyelet body 180 is a hole, through which a knotted suture 256 will exit. The knotted suture 256 functions to fix a distal end of a tensionable suture loop to the anchor body 120. A tensionable suture loop as part of the assembly construct may be provided by including a pre-threaded tensionable suture loop, so as to provide a construct assembly having a "pre-looped" tensionable loop. Alternatively, a tensionable loop that is not pre-threaded may be included with the assembly construct, so as to provide a "non-pre-looped" tensionable loop version of the assembly construct. In the non-pre-looped tensionable loop construct assembly configuration, the tensionable loop will be formed after the anchor body 120 has been inserted into a surface, such as inserted into bone. The driver and anchor assembly would take on the same general appearance in both the pre-looped and non-pre-looped tensionable loop construct assembly. Knotted suture end 256 exiting the hole in the side of the eyelet body 180 of the tip 190, serves to fix a distal strand of a tensionable loop (either pre-looped or non-pre-looped tensionable loop construct), to the anchor body 120. An eyelet 160 is provided within the eyelet body 180 of the tip 190.

Figure 36A:
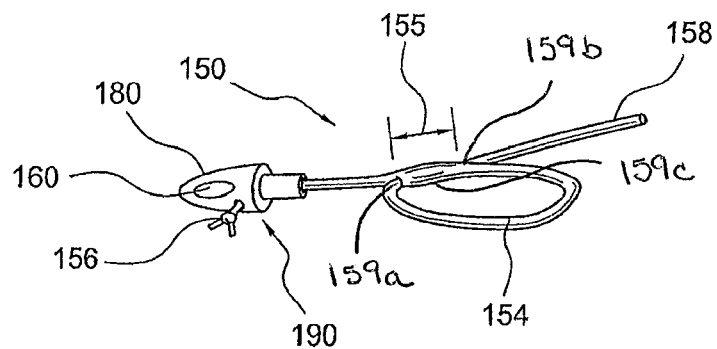
FIGS. 36A and 36B illustrates a pre-looped tensionable loop assembly and a non-pre-looped tensionable loop assembly, respectively.
Figure 36B:
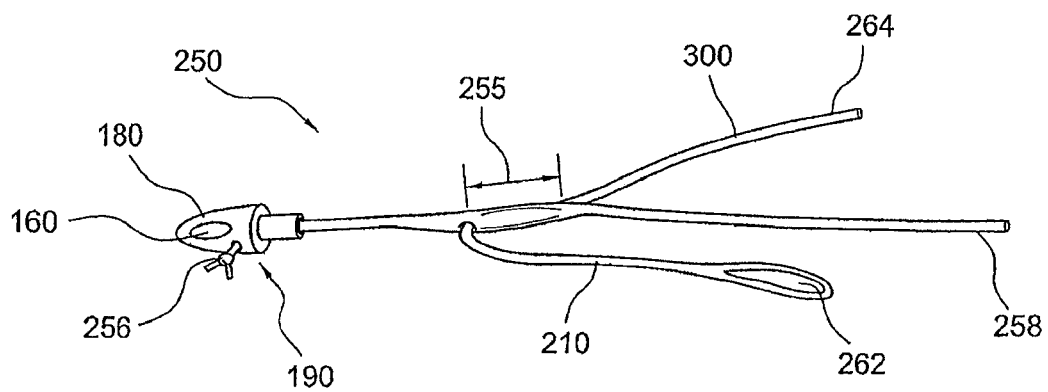

FIG. 36A illustrates a pre-looped tensionable loop assembly 150 and FIG. 36B illustrates a non-pre-looped tensionable loop assembly 250. The pre-looped tensionable loop assembly 150 includes a tensionable loop 154 that has been pre-threaded through a splice region 155. Knotted suture end 156 at the eyelet body 180 serves to fix the distal strand of the tensionable loop 154 within a suture anchor.

FIG. 36B illustrates the non-pre-looped tensionable loop assembly 250 that includes a looped end 262 of a passing strand 210 (passing strand may be a FiberLink passer strand or a Nitinol wire passer strand). The free end 264 of the passing strand and the main fixation suture limb 258 are provided as part of the non-pre-looped tensionable loop assembly. The main fixation suture limb 258 will be threaded through a splice region 255 of the suture after passing the suture limb 258 through the soft tissue that is to be secured. A knotted suture end 256 at the eyelet body 180 serves to fix a distal end of the tensionable loop once formed.

Figure 37A:
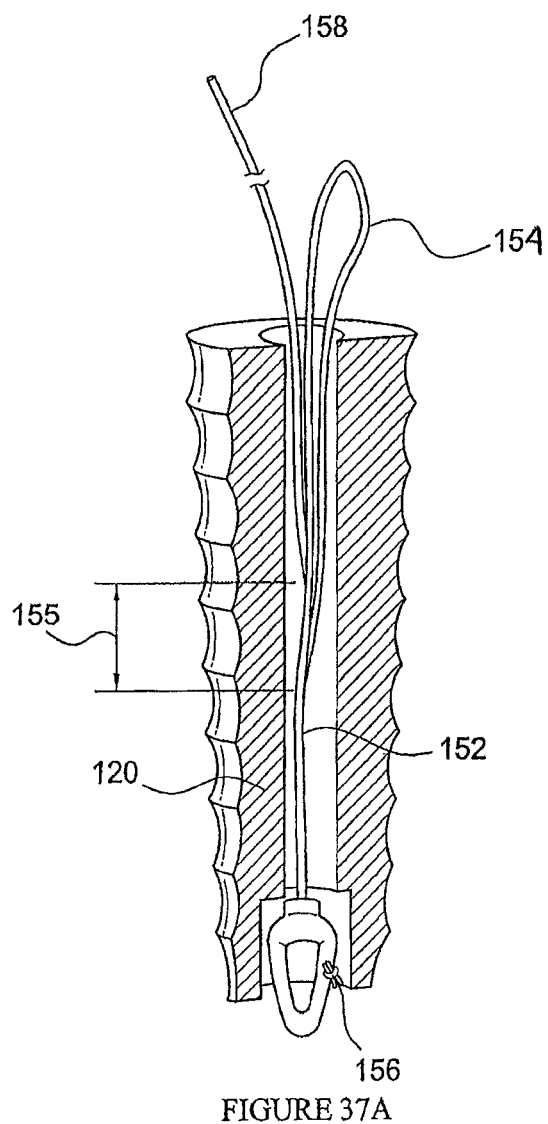
Figure 37B:
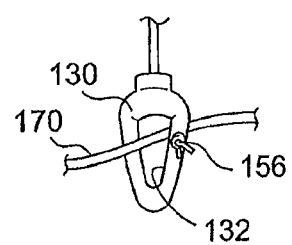

FIG. 37A illustrates the suture anchor and tensionable loop (pre-looped tensionable loop version) construct configuration after the suture anchor 150 has been inserted into a surface, such as into a bone. FIG. 37B presents the eyelet body 130 that includes an eyelet 132, through which a suture limb 170 is passed. Also depicted is the knotted suture end 156 present on the suture body 130.

FIG. 37C illustrates the suture anchor and tensionable loop (non-pre-looped tensionable loop version) construct configuration 250 after the suture anchor 220 has been inserted into a surface, such as into a bone. The main fixation suture 258 will be threaded through the splice region 255 of the suture 252, after the main fixation suture is passed through or around an adjacent or surrounding penetrable material, such as through or around a soft tissue. The free passing end 264 of the passing strand is shown extending out of the suture anchor shaft 350 of the suture anchor 220. The looped end 262 of the passing strand is also shown extending out of the suture anchor shaft 350 of the suture anchor 220. The passing strand may be of a FiberLink passer material or a nitinol wire passer material. An eyelet 232 is provided at a tip 190 provided as part of the construct configuration, and includes an eyelet body 230. Located on the eyelet body 230 is a knotted suture end 256. FIG. 37D illustrates a detailed view of the tip 190. The tip 190 is shown to include an eyelet body 230 and an eyelet 232, through which a suture 172 may be passed. A knotted suture end 256 is shown at the eyelet body 230. The knotted suture end 256 of the passing suture strand serves to fix the distal end of the tensionable loop, and to maintain a continued tension between the suture and suture anchor after the suture anchor is implanted. This continued tension serves to enhance the self-locking mechanism at the suture splice 255.

A surgical kit is disclosed that may include one or more of the fixation devices 102 and 202 preloaded with the tensionable pre-looped and tensionable non-pre-looped constructs 150 and 152, respectively. One or more of the additional fixation devices 302 may also be provided with the kit along with the optional cannula 300.

Figure 38:
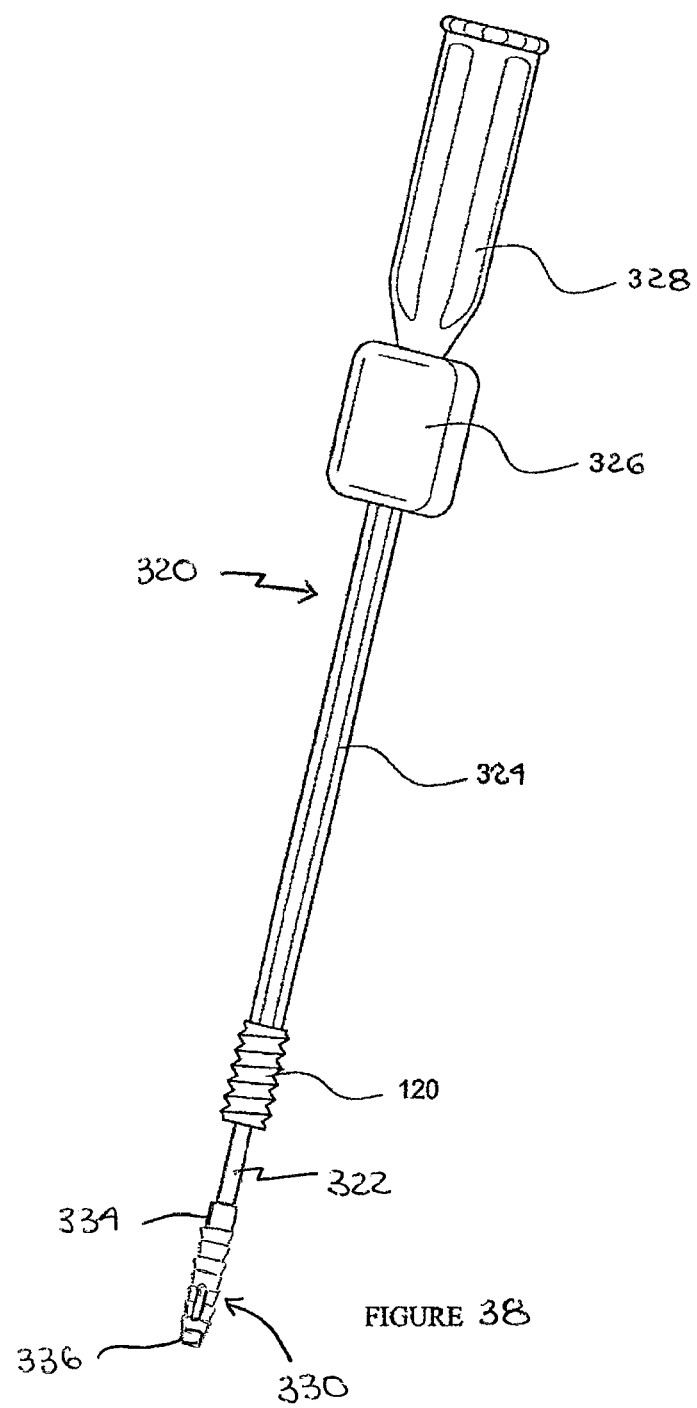
FIG. 38 illustrates another driver and anchor assembly.
Figure 39A:
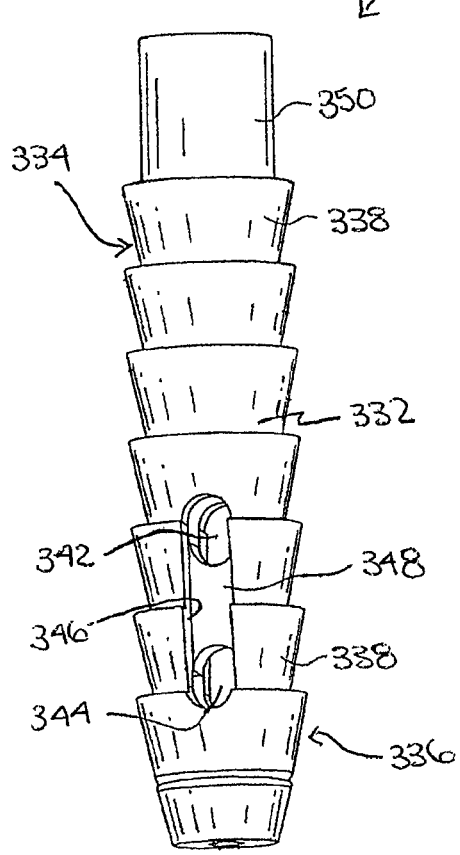
FIGS. 39A and 39B are elevational and cross-sectional views, respectively, of a tip of the assembly illustrated in FIG. 38.
Figure 39B:
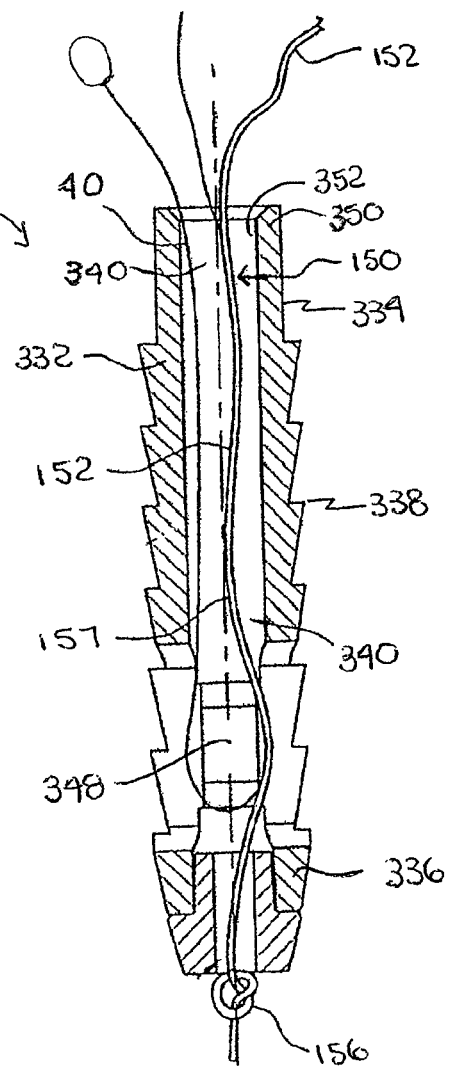
Figure 40:
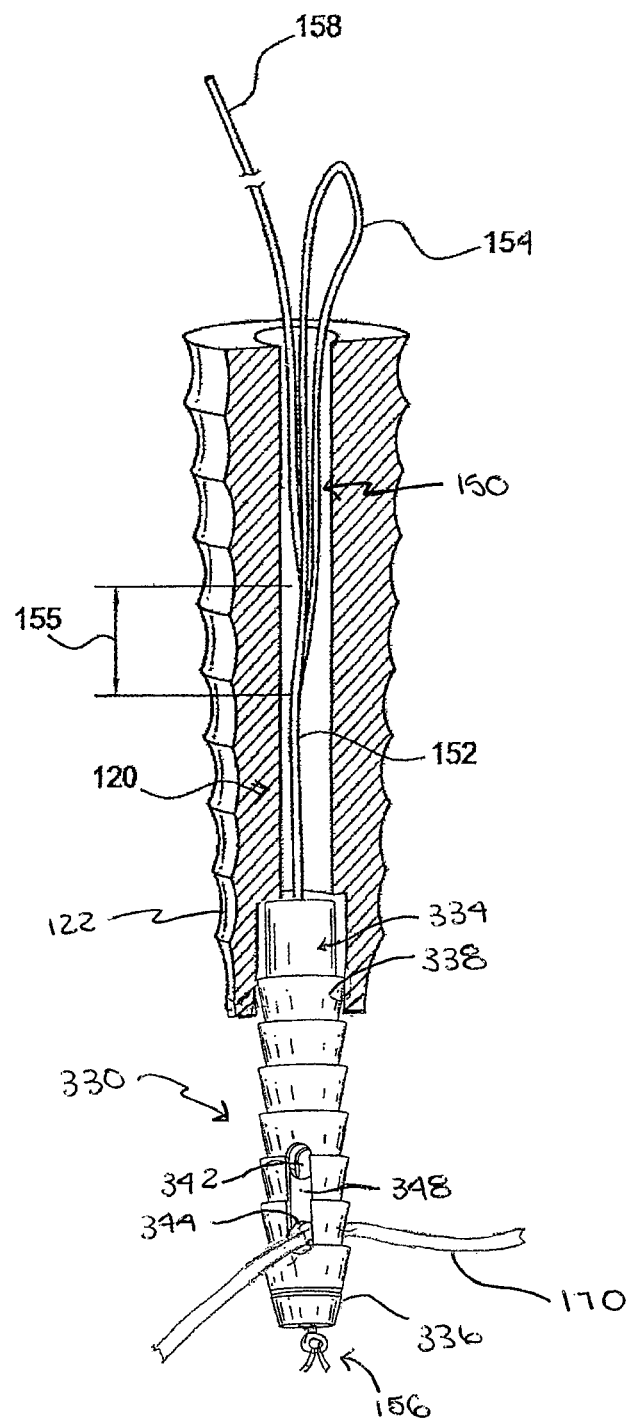
FIG. 40 illustrates an anchor construct loaded onto the anchor assembly illustrated in FIG. 38, depicted after the anchor has been inserted into the bone.

FIGS. 38-40 illustrate another driver and anchor assembly, and methods of tissue repair using the same, that may include the same or similar anchor body 120, as described above, and an alternative anchor tip 330. Similar to the embodiments above, the anchor body 120 is configured to be insertable over an end portion of the anchor tip 330. The tensionable construct 150 may be pre-loaded on the tip 330 to form the surgical assembly. In some embodiments, the flexible material 170 may also be pre-loaded onto the tip 330.

Anchor tip 330 may be similar to the anchor disclosed in commonly assigned U.S. Pat. No. 9,855,029, the subject matter of which is herein incorporated by reference. As seen in FIGS. 39A and 39B, tip 330 may comprise a body 332 that has a proximal end 334 and a distal end 336, and a plurality of ribs 338 extending outwardly and circumferentially around the body 332. A cannulation 340 extends along an inside of the body 332 to allow passage of the construct 150 and optionally a suture passing device 40. Openings 342 and 344 may be located on either side of a portion 348 of the body 332 to allow threading of the flexible strand 152 of the construct 150 around the portion 348, which may be an inner post, for example, as best seen in FIG. 39A.

Proximal end 334 of the tip's body 332 may have a driver engagement portion 350 configured for insertion into the distal end 122 of anchor body 120 and can have an inner socket 352 configured to engage the distal end of the rod 306 of the driver. In some embodiments, proximal end 334 of the tip's body 332 can instead be sized to fit inside the distal end of the rod 306 of the driver. Openings 342 and 344 can extend in a direction generally perpendicular to the longitudinal axis L of the body 332 and communicate through respective recesses 346 with the outer surface of tip's body 332. Recesses 346 may be located on the opposite sides of tip's body 332. And recesses 346 can be positioned opposite to each other relative to the post 348 and can be symmetrically located relative to the post 348, to allow flexible strand 152 of the tensionable construct 150 and optionally the shuttle/pull device 40 to pass and slide therethrough. In an embodiment, one of the openings 342 and 344, and preferably opening 344 near the distal end 336 of the body 332, accommodates the flexible member 170. The position and size of the openings 342 and 344 and the recesses 346 may be determined according to the characteristics of the flexible strand 152, the shuttle/pull device 40, the flexible material 170, and/or according to the arthroscopic procedure, and the need to precisely orientate the anchor during insertion to optimize suture sliding characteristics.

The tensionable construct 150 (either pre-looped or non-pre-looped tensionable construct) can include splice 155 for forming the tensionable loop 154, as seen in FIGS. 36A and 40. In an embodiment, the splice 155 may be formed by two apertures 159a and 159b at different locations along the length of the flexible strand 152 and a channel 159c extending though the flexible strand 152 connecting the two apertures 159a and 159b, as seen in FIG. 36A. The channel 159c may, for example, form a coreless portion of the flexible strand 152. A passer device, such as passer 260 may be pre-loaded on construct 150 by threading the passer through the splice 155. The construct 150 can be connected to the distal end 336 of the tip 330, for example, by knotted end 156 of construct 150. The knotted end 156 may be positioned at the tip's distal end 336 just outside of cannulation 340, thereby fixing the end 157 (FIG. 39B) of the flexible strand 152, that is opposite its free end 158, to the tip 330. Flexible strand 152 may pass around or along post 348, which can be large enough to allow suture 152 to take gradual turns instead of sharp turns. Strand 152 then passes through cannulation 340 and exits at the proximal end 334 of the tip 330. In an embodiment, post 348 can be positioned between two portions of the flexible strand 152, such that those two portions can wrap around post 348 and are configured to extend away from the tip's distal end 336. For example, after tensionable loop 154 has been formed, flexible strand 152 extends around post 348, with two portions of flexible strand 152 respectively extending on either side of post 348 towards the proximal end 334 of the tip 330.

FIG. 38 illustrates the driver and anchor assembly with tip 330 prior to implementation and installation in the bone hole and FIG. 40 illustrates the anchor assembly after insertion into the bone hole. Anchor body 120, via its cannulation, receives and is seated on the cannulated rod 322 of the driver 320, and the anchor tip 330 is seated at the distal end of the rod 322. The reverse threaded sleeve 324 serves to drive the anchor body 120 into the bone hole, in a similar manner as described above. Thumb pad 326 and the handle 328 may be used to assist with driving the anchor assembly. The tip 330 can be located at the distal end of the anchor assembly opposite the handle 328, as seen in FIG. 38, such that the end of the driver's rod 322 engages with the inner socket 352 of tip 330, or otherwise engages with the proximal end 334 of tip 330.

During installation of the anchor assembly, anchor tip 330 can be placed within the prepared bone hole until anchor tip 330 reaches the bottom of the bone hole, or reaches the desired depth in the bone hole, while the anchor body 120 resides on the driver's rod 322 outside of the bone hole. Anchor body 120 can then be advanced down rod 322 by holding thumb pad 326 as the handle 328 of the driver is turned clockwise so that the anchor body 120 advances over at least a portion of tip 330 to seat thereon. In an embodiment, when anchor body 120 is seated on tip 330, the distal end 122 of anchor body 120 fits over the driver engagement 350 at the proximal end 334 of tip 330, and in some embodiments, may also cover one or more ridges 338 of the tip's body 332, as seen in FIG. 40, to create a stable swivel connection therebetween.

In an exemplary method of stabilizing a bone or joint lesion, two or more of the disclosed fixation devices or anchor assemblies may be used for the tissue repair. The method may include, for example, implanting the first fixation device into a first bone hole by inserting the tip 330 thereof in the first bone hole and thereafter separately securing the anchor body 120 to the tip 330 in the first bone hole, with the tensionable construct 150 extending into and through the anchor body 120; and implanting a second fixation device into a second bone hole in a similar manner as the first fixation device. The free ends 158 of the flexible strands 152 of the two fixation devices may then be passed through different locations of tissue. The free end 158 of the flexible strand 152 of the first fixation device can be passed through the splice 155 of the flexible strand of the second fixation device, and vice versa, that is the free end 158 of the flexible strand 152 of the second fixation device can be passed through the splice 155 of the flexible strand of the first fixation device. The method may also include pulling each of the free ends 158 of the flexible strands 152 after passing the respective free ends through the respective splices of each of the fixation devices, such that the flexible strands 152 of both the first and second fixation devices compress the tissue between the first and second bone holes relative to the bone. Other fixation methods may also be employed using these similar fixation devices.

In an embodiment of the method, each of the fixation devices may further comprise a flexible material 170 that may be held in the opening 344 of tip 330, wherein the flexible material 170 is separate from the tensionable construct 150 and is configured to form at least one further connection separate from the connections formed by the flexible strands 152 of the first and second fixation devices. In other embodiments, the flexible material 170 may be attached to the tip 330 in other ways. For example, in some embodiments, the tip 330 may be modified to include an additional eyelet at or near its distal end 336 that is separate from openings 342, 344, for the flexible material 170 to be threaded through. In still other embodiments, an additional eyelet or opening can also be formed in other portions of the tip 330 and/or in other manners on or in the tip 330. In yet another variation, as can be seen most clearly in FIG. 39B, there are multiple existing sutures, passing devices, etc., that extend from the proximal end 334 of tip 330 prior to implantation. These sutures can also be used to thread and temporarily hold the flexible material 170, where the flexible material 170 can be passed between two of the sutures in an initial configuration. Then, when the anchor body 120 is advanced and assembled to the tip 330 (as seen in FIG. 40), the flexible material 170 will be pinched between the anchor body 120 and tip 330, and thereby held in place for additional connections. The method may further comprise securing respective first sections or limbs 170a of the flexible material 170 of the first and second fixation devices to a third fixation device and securing the third fixation device into a third bone hole, and in some embodiments, likewise securing respective second sections or limbs 170b of the flexible material 170 of the first and second fixation devices to a fourth fixation device and securing the fourth fixation device into a fourth bone hole. More or less fixation devices and securing methods are also envisioned.

While particular embodiments have been chosen to illustrate the invention, it will be understood by those skilled in the art that various changes and modifications can be made therein without departing from the scope of the invention as defined in the appended claims.

What is claimed is:

1. A device for tissue repairs, comprising:
   an anchor body comprising a central shaft and an outer surface having a fixation structure for securing the anchor body in a bone hole;
   a tip having a first end, a second end, a longitudinal axis extending between the first and second ends, and an opening or recess extending transverse to the longitudinal axis, wherein the first end of the tip is separable from and connectable to the anchor body;
   a tensionable construct fixedly connected to the tip and comprising a flexible strand defining two apertures at different locations along a length of the flexible strand, and a channel extending through the flexible strand and connecting the two apertures, for forming a splice and a loop with an adjustable perimeter adjacent the splice; and
   a flexible member different from the tensionable construct that is releasably held in the opening or recess of the tip, wherein when the tip is connected to the anchor body and the flexible member is held in the opening or recess, the tensionable construct is configured to extend through the anchor body while the flexible member remains entirely outside of the anchor body;
   wherein a portion of the tip is positionable between two portions of the flexible strand in a direction perpendicular to the longitudinal axis, and wherein the two portions of the flexible strand are configured to extend away from the second end of the tip.

2. The device of claim 1, wherein the first end of the tip is connectable to the anchor body such that at least part of the opening or recess is unobstructed by the anchor body in a transverse direction that is transverse to the longitudinal axis for the flexible member to extend therethrough without extending through the anchor body.

3. The device of claim 1, wherein the two portions of the flexible strand are configured to be connected to one another in a region between the portion of the tip and the second end of the tip.

4. The device of claim 3, wherein the portion of the tip comprises a post, and wherein the flexible strand is configured to extend around a side of the post closest to the second end.

5. The device of claim 4, wherein the two portions of the flexible strand are further configured to be connected to one another on a side of the post closest to the first end.

6. The device of claim 1, wherein the channel through the flexible strand forms a coreless portion of the flexible strand.

7. The device of claim 1, wherein the flexible strand of the tensionable construct is configured to extend through the anchor body.

8. The device of claim 1, wherein the flexible strand further comprises the splice formed at the channel and the loop, wherein the loop is a knotless, tensionable, self-cinching loop with the adjustable perimeter.

9. The device of claim 8, wherein when the knotless, tensionable, self-cinching loop is formed, two separate segments of the flexible strand extend around the tip between the portion of the tip and the second end of the tip.

10. The device of claim 1, wherein the flexible strand further comprises a free end at a side opposite the fixed connection.

11. The device of claim 10, wherein the splice and loop are formed by threading the free end of the flexible strand through the channel of the flexible strand, wherein the loop formed is a knotless, tensionable, self-cinching loop with the adjustable perimeter, and wherein the free end of the flexible strand forms a tensioning suture limb for reducing the perimeter of the knotless, tensionable, self-cinching loop.

12. The device of claim 1, wherein the fixation structure on the outer surface of the anchor body comprises a thread, ribs, ridges, and/or barbs.

13. The device of claim 1, wherein the tip and the anchor body are rotatable relative to one another when the first end of the tip is connected to the anchor body, such that the tip and the anchor body together form a swivel anchor.

14. The device of claim 1, wherein the opening or recess forms an eyelet that extends through the tip.

15. The device of claim 1, wherein the first end of the tip is insertable into the anchor body.

16. The device of claim 1, further comprising a passer device pre-loaded through the channel of the flexible strand, wherein both ends of the passer device are configured to extend through the anchor body.

17. The device of claim 1, wherein the tensionable construct is fixedly connected to the tip prior to the splice and the loop with the adjustable perimeter being formed.

18. The device of claim 1, wherein a knotted end of the tensionable construct fixedly connects the tensionable construct to the tip.

* * * * *